United States Patent [19]

Kamiya et al.

[11] 4,214,094
[45] Jul. 22, 1980

[54] SUBSTITUTED-PHENYL SUBSTITUTED-ALKYL ETHERS AND THE PREPARATION THEREOF

[75] Inventors: Takashi Kamiya, Suita; Yoshihisa Saito, Takarazuka, both of Japan

[73] Assignee: Fujisawa Pharmaceutical Co., Ltd., Osaka, Japan

[21] Appl. No.: 782,967

[22] Filed: Mar. 30, 1977

Related U.S. Application Data

[63] Continuation-in-part of Ser. No. 583,474, Jun. 3, 1975, abandoned.

[51] Int. Cl.$^2$ .................. C07C 101/72; A61K 31/24
[52] U.S. Cl. .................. 560/42; 260/326.8; 260/570.9; 424/309; 424/319; 560/45; 562/451; 562/452; 548/161; 546/312
[58] Field of Search .................. 260/519, 42; 560/42, 560/45; 562/451, 452

[56] References Cited

U.S. PATENT DOCUMENTS

| | | | |
|---|---|---|---|
| 3,369,025 | 2/1968 | Bolhofer | 562/431 |
| 3,781,328 | 12/1973 | Witte et al. | 560/42 |
| 3,906,032 | 9/1975 | Hauck | 260/519 |
| 4,010,279 | 3/1977 | Griss et al. | 560/42 |
| 4,042,711 | 8/1977 | Griss et al. | 562/451 |

FOREIGN PATENT DOCUMENTS

| | | |
|---|---|---|
| 829791 | 6/1975 | Belgium . |
| 2405622 | 8/1975 | Fed. Rep. of Germany ............ 260/519 |
| 2524865 | 1/1976 | Fed. Rep. of Germany ............ 560/42 |

OTHER PUBLICATIONS

Biryakov et al., "Chem. Abstracts", 15377(w) vol. 76, 1972.
Witte et al., "Chem. Abstracts", 121481(a) vol. 84, 1976.

*Primary Examiner*—Bernard Helfin
*Assistant Examiner*—G. T. Breitenstein
*Attorney, Agent, or Firm*—Dayton R. Stemple, Jr.

[57] ABSTRACT

The present invention relates to new substituted-phenyl substituted-alkyl ethers and pharmaceutically acceptable salts thereof, which have hypolipidemic activity, and to processes for the preparation thereof, the compound having the following formula

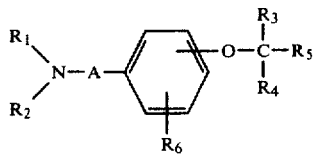

wherein $R_1$ is lower alkyl, cycloalkyl, aryl, ar(lower)alkyl, a heterocyclic group or a group represented by the formula:

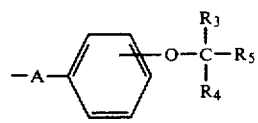

wherein
$R_3$ and $R_4$ are each hydrogen or lower alkyl,
$R_5$ is carboxy, esterified carboxy or hydroxymethyl and A is lower alkylene;
$R_2$ is hydrogen, lower alkyl, cycloalkyl, aryl, ar(lower)alkyl, a heterocyclic group or a group represented by the formula:

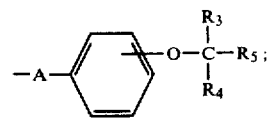

and
$R_6$ is hydrogen, hydroxy or lower alkoxy; in which the aryl or the ar(lower)alkyl for $R_1$ and $R_2$ may be substituted with halogen, hydroxy or lower alkoxy, and when $R_1$ and $R_2$ are both lower alkyl, $R_1$ and $R_2$ may be linked together.

45 Claims, No Drawings

SUBSTITUTED-PHENYL SUBSTITUTED-ALKYL ETHERS AND THE PREPARATION THEREOF

This application is a continuation-in-part of Ser. No. 583,474, filed June 3, 1975, now abandoned.

The present invention relates to new substituted-phenyl substituted-alkyl ethers and pharmaceutically acceptable salts thereof, which have hypolipidemic acivity, and to processes for the preparation thereof.

The new substituted-phenyl substituted-alkyl ethers of the present invention are represented by the formula:

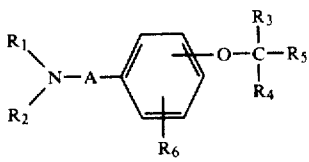

wherein $R_1$ is lower alkyl, cycloalkyl, aryl ar(lower)alkyl, a heterocyclic group or a group represented by the formula:

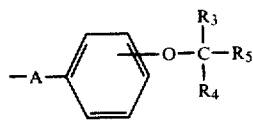

wherein $R_3$ and $R_4$ are each hydrogen or lower alkyl, $R_5$ is carboxy, esterified carboxy or hydroxymethyl and A is lower alkylene;

$R_2$ is hydrogen, lower alkyl, cycloalkyl, aryl, ar(lower)alkyl, a heterocyclic group or a group represented by the formula:

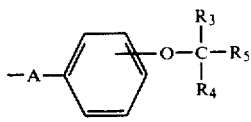

wherein $R_3$, $R_4$, $R_5$ and A are each as defined above; $R_3$, $R_4$, $R_5$ and A are each as defined above; and $R_6$ is hydrogen, hydroxy or lower alkoxy; in which the aryl or the ar(lower)alkyl for $R_1$ and $R_2$ may be substituted with halogen, hydroxy or lower alkoxy, and when $R_1$ and $R_2$ are both lower alkyl, $R_1$ and $R_2$ may be linked together.

In this specification, it is to be understood that the term "lower" used in connection with the moieties derived from alkane such as alkyl or alkylene is intended to mean a group having 1 to 6 carbon atom(s) unless otherwise indicated.

The suitable example of lower alkyl may be one having 1 to 6 carbon atom(s) such as methyl, ethyl, propyl, isopropyl, butyl, isobutyl, tert-butyl, pentyl, hexyl or the like, and preferably one having 1 to 4 carbon atom(s).

The suitable example of cycloalkyl may be one having 3 to 7 carbon atoms such as cyclopropyl, cyclobutyl, cyclopentyl, cyclohexyl, cycloheptyl or the like, and preferably one having 4 to 6 carbon atoms.

The suitable example of aryl may be one having 6 to 10 carbon atoms such as phenyl, tolyl, xylyl, mesityl, cumenyl, naphthyl or the like, and preferably one having 6 to 8 carbon atoms.

The suitable example of ar(lower)alkyl may be one having 7 to 10 carbon atoms such as benzyl, phenethyl, tolylmethyl, xylylmethyl, mesitylmethyl, cumenylmethyl or the like, and preferably one having 7 to 8 carbon atoms.

The aryl or ar(lower)alkyl mentioned above may be optionally substituted with halogen (e.g., chlorine, bromine, fluorine or iodine), hydroxy or lower alkoxy, wherein such substituents may be same or different ones more than 2.

The suitable example of lower alkoxy may be one having 1 to 6 carbon atom(s), such as methoxy, ethoxy, propoxy, isopropoxy, butoxy, isobutoxy, tert-butoxy, pentyloxy, hexyloxy or the like, and preferably one having 1 to 4 carbon atom(s), and more preferably one having 1 to 2 carbon atom(s).

The heterocyclic group includes mono- or polycyclic heterocyclic groups which contain at least one hetero atom selected from the group consisting of oxygen, sulfur, nitrogen and the like. The suitable example of the heterocyclic groups may be 3 to 8-membered heteromonocycle containing a sulfur atom (e.g. thienyl, etc.), a condensed-heterocycle containing a sulfur atom (e.g. benzothienyl, etc.), a 3 to 8-membered heteromonocycle containing an oxygen atom (e.g. furyl, pyranyl, etc.), a condensed-heterocycle containing an oxygen atom (e.g. isobenzofuranyl, chromenyl, xanthenyl, etc.), a 3 to 8-membered heteromonocycle containing 1 to 4 nitrogen atom(s) (e.g. 2H-pyrrolyl, 3H-pyrrolyl, pyrrolyl, pyrrolinyl, imidazolyl, pyrazolyl, pyridyl, pyrimidinyl, pyrazinyl, pyridazinyl, diazolyl, triazolyl, tetrazolyl, etc.), a condensed-heterocycle containing 1 to 3 nitrogen atom(s) (e.g. indolyl, isoindolyl, indazolyl, quinolyl, isoquinolyl, benzotriazolyl, benzimidazolyl, etc.), a 3 to 8-membered heteromonocycle containing an oxygen atom and 1 to 3 nitrogen atom(s) (e.g. oxazolyl, isoxazolyl, oxadiazolyl, etc.), a condensed-heterocycle containing an oxygen atom and 1 to 2 nitrogen atom(s) (e.g. benzoxazolyl, benzoxadiazolyl, etc.), a 3 to 8-membered heteromonocycle containing a sulfur atom and 1 to 3 nitrogen atom(s) (e.g. thiazolyl, isothiazolyl, thiadiazolyl, etc.), a condensed-heterocycle containing a sulfur atom and 1 to 2 nitrogen atom(s) (e.g. benzothiazolyl, benzothiadiazolyl, etc.), and the like.

The suitable example of esterified carboxy may be, for example, lower alkoxycarbonyl having 2 to 7 carbon atoms such as methoxycarbonyl, ethoxycarbonyl, propoxycarbonyl, isopropoxycarbonyl, butoxycarbonyl, tert-butoxycarbonyl, pentyloxycarbonyl or the like, and preferably one having 2 to 4 carbon atoms; cycloalkoxycarbonyl having 6 to 8 carbon atoms such as cyclopentyloxycarbonyl, cyclohexyloxycarbonyl, cycloheptyloxycarbonyl or the like; lower alkenyloxycarbonyl having 3 to 6 carbon atoms such as vinyloxycarbonyl, 1-propenyloxycarbonyl, allyloxycarbonyl, 1,1-dimethyl-2-propenyloxycarbonyl, 3-butenyloxycarbonyl or the like; lower alkynyloxycarbonyl having 4 to 6 carbon atoms such as 2-propynyloxycarbonyl, 1,1-dimethyl-2-propynyloxycarbonyl or the like; aryloxycarbonyl having 7 to 11 carbon atoms such as phenoxycarbonyl, tolyloxycarbonyl, xylyloxycarbonyl, naphthyloxycarbonyl or the like; ar(lower)alkoxycarbonyl having 8 to 10 carbon atoms such as benzyloxycarbonyl, phenethyloxycarbonyl, tolylmethoxycarbonyl, xylylmethoxycarbonyl or the like; lower alkoxy(lower)alkoxycarbonyl having 3 to 5 carbon atoms such as methoxymethoxycarbonyl, ethoxymethoxycarbonyl, ethoxyethoxycarbonyl or the like; lower alkylthio(lower)alkoxycarbonyl having 3 to 5 carbon atoms such as methylthiomethoxycarbonyl, methylthioethoxycarbonyl, ethylthioethoxycarbonyl or the like; di(lower)alkylamino(lower)alkoxycarbonyl having 4 to 7 carbon atoms such as dimethylaminomethoxycarbonyl, dimethylaminoethoxycarbonyl, diethylaminoethoxycarbonyl or the like; aryloxy(lower)alkoxycarbonyl having 8 to 9 carbon atoms such as phenoxymethoxycarbonyl, phenoxyethoxycarbonyl or the like; arylthio(lower)alkoxycarbonyl having 8 to 9 carbon atoms such as phenylthiomethoxycarbonyl, phenylthioethoxycarbonyl or the like; aroyl(lower)alkoxycarbonyl having 9 to 10 carbon atoms such as benzoylmethoxycarbonyl, toluoylmethoxycarbonyl or the like; lower alkaneamido(lower)alkoxycarbonyl having 4 to 5 carbon atoms such as acetamidomethoxycarbonyl, acetamidoethoxycarbonyl or the like; or esters formed by the reaction of carboxy group with 3-hydroxypyridine, 3-hydroxymethylpyridine, 2-hydroxymethylpyridine-1-oxide, 1-methyl-4-hydroxypiperidine, 1,3-propanediol or the like.

The suitable example of lower alkylene may be one having 1 to 4 carbon atom(s) such as methylene, ethylene, methylethylene, propylene, trimethylene, 2-methyltrimethylene or the like, and preferably one having 1 to 2 carbon atom(s).

In the above definition, when $R_1$ and $R_2$ are both lower alkyl, $R_1$ and $R_2$ may be linked together to form a ring containing a nitrogen atom such as pyrrolidinyl, piperidino, homopiperidino or the like.

The suitable example of pharmaceutically acceptable salts may be salts with an acid such as an inorganic acid (e.g., hydrochloric acid, hydrobromic acid, sulfuric acid, etc.), an organic acid (e.g., acetic acid, maleic acid, fumaric acid, tartaric acid, benzenesulfonic acid, toluenesulfonic acid, etc.) or the like; and salts with a base, i.e. an inorganic base, for example, an alkali metal salt (e.g., sodium salt, potassium salt, etc.), an alkaline earth metal salt (e.g., calcium salt, magnesium salt, etc.), a salt with an organic base (e.g., triethylamine, pyridine, N,N-dimethylaniline, etc.) or the like.

The object compound (I) of the present invention may be prepared by various methods and these methods are illustrated as follows:

Process A:

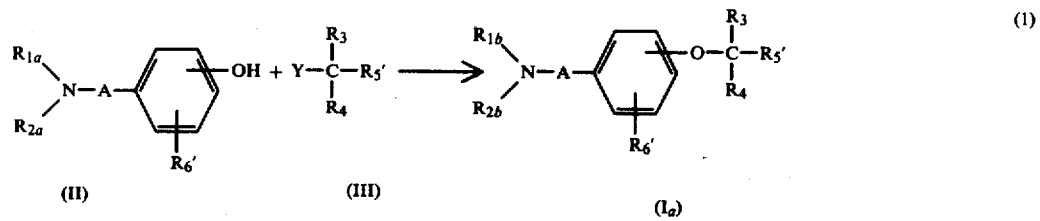

Process B:

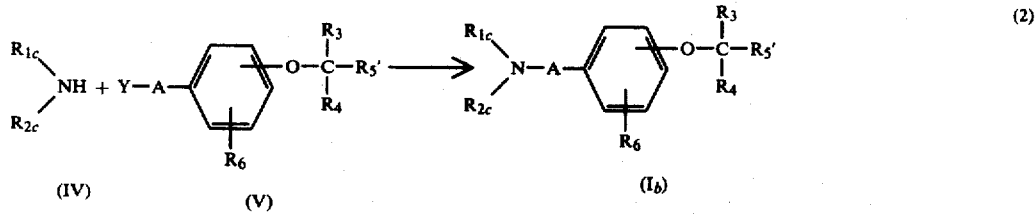

Process C:

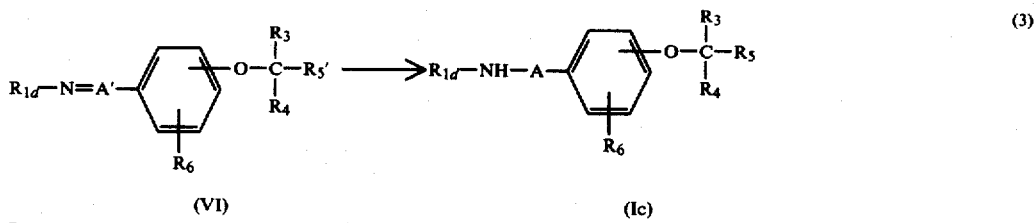

Process D:

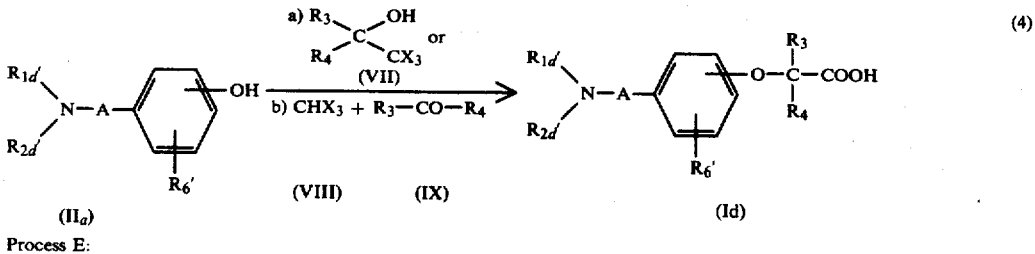

Process E:

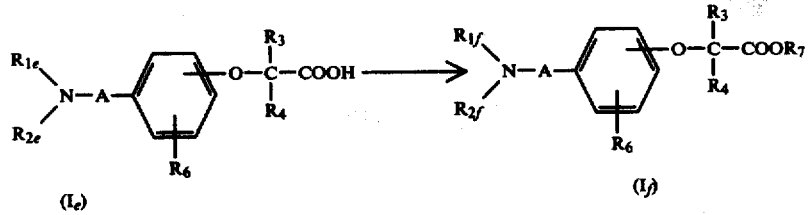
(5)

Process F:

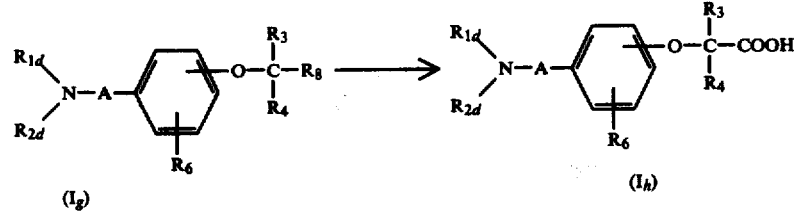
(6)

Process G:

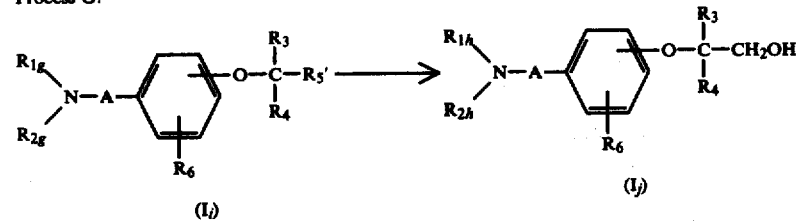
(7)

Process H:

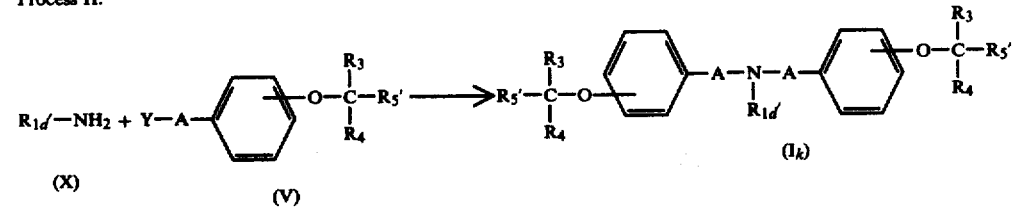
(8)

Process I:

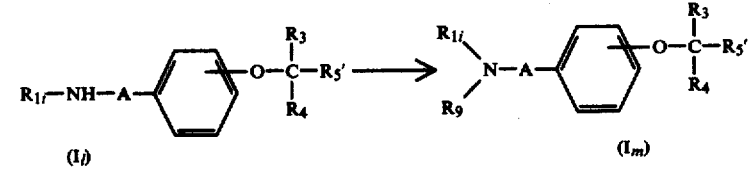
(9)

Process J:

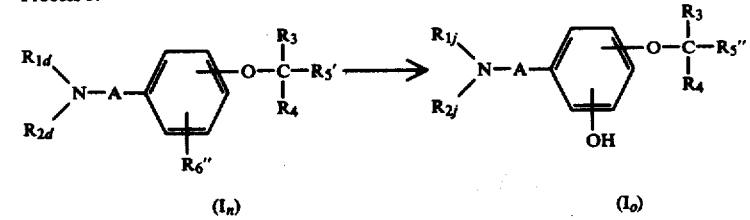
(10)

in which $R_1$, $R_2$, $R_3$, $R_4$, $R_5$, $R_6$ and A are each as defined above;

$R_{1a}$ is lower alkyl, cycloalkyl, aryl, ar(lower)alkyl, a heterocyclic group or a group represented by the formula:

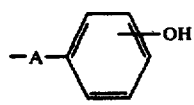

wherein A is as defined above;

$R_{2a}$ is hydrogen, lower alkyl, cycloalkyl, aryl, ar(lower)alkyl, a heterocyclic group or a group represented by the formula:

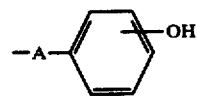

wherein A is as defined above, in which the aryl or the ar(lower)alkyl for $R_{1a}$ and $R_{2a}$ may be substituted with halogen or lower alkoxy, and when $R_{1a}$ and $R_{2a}$ are both lower alkyl, $R_{1a}$ and $R_{2a}$ may be linked together, $R_6'$ is hydrogen or lower alkoxy;

Y is an acid residue;

$R_5'$ is carboxy or esterified carboxy;

$R_{1b}$ is lower alkyl, cycloalkyl, aryl, ar(lower)alkyl, a heterocyclic group or a group represented by the formula:

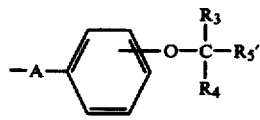

wherein $R_3$, $R_4$, $R_5'$ and A are each as defined above;

$R_{2b}$ is hydrogen, lower alkyl, cycloalkyl, aryl, ar(lower)alkyl, a heterocyclic group or a group represented by the formula:

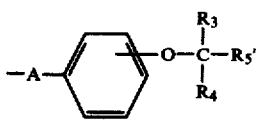

wherein $R_3$, $R_4$, $R_5'$ and A are each as defined above, in which the aryl or the ar(lower)alkyl for $R_{1b}$ and $R_{2b}$ may be substituted with halogen or lower alkoxy, and when $R_{1b}$ and $R_{2b}$ are both lower alkyl, $R_{1b}$ and $R_{2b}$ may be linked together;

$R_{1c}$ is lower alkyl, cycloalkyl, aryl, ar(lower)alkyl or a heterocyclic group;

$R_{2c}$ is hydrogen, lower alkyl, cycloalkyl, aryl, ar(lower)alkyl or a heterocyclic group, in which the aryl or the ar(lower)alkyl for $R_{1c}$ and $R_{2c}$ may be substituted with halogen, hydroxy or lower alkoxy, and when $R_{1c}$ and $R_{2c}$ are both lower alkyl, $R_{1c}$ and $R_{2c}$ may be linked together;

A' is a trivalent residue of saturated aliphatic hydrocarbon group, $R_{1d}$ is lower alkyl, cycloalkyl, aryl or ar(lower)alkyl, in which the aryl or the ar(lower)alkyl for $R_{1d}$ may be substituted with halogen, hydroxy or lower alkoxy;

$R_{1d}'$ is lower alkyl, cycloalkyl, aryl or ar(lower)alkyl;

$R_{2d}'$ is hydrogen, lower alkyl, cycloalkyl, aryl or ar(lower)alkyl, in which the aryl or the ar(lower)alkyl for $R_{1d}'$ and $R_{2d}'$ may be substituted with halogen or lower alkoxy, and when $R_{1d}'$ and $R_{2d}'$ are both lower alkyl, $R_{1d}'$ and $R_{2d}'$ may be linked together;

X is halogen;

$R_{1e}$ is lower alkyl, cycloalkyl, aryl, ar(lower)alkyl or a group represented by the formula:

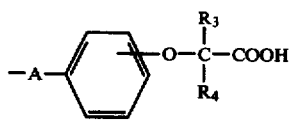

wherein $R_3$, $R_4$ and A are each as defined above;

$R_{2e}$ is hydrogen, lower alkyl, cycloalkyl, aryl, ar(lower)alkyl or a group represented by the formula:

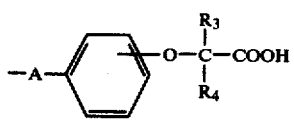

wherein $R_3$, $R_4$ and A are each as defined above, in which the aryl or the ar(lower)alkyl for $R_{1e}$ and $R_{2e}$ may be substituted with halogen, hydroxy or lower alkoxy, and when $R_{1e}$ and $R_{2e}$ are both lower alkyl, $R_{1e}$ and $R_{2e}$ may be linked together;

$R_{1f}$ is lower alkyl, cycloalkyl, aryl, ar(lower)alkyl or a group represented by the formula:

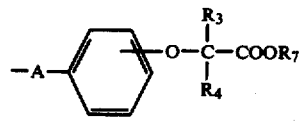

wherein $R_3$, $R_4$ and A are each as defined above and $R_7$ is lower alkyl;

$R_{2f}$ is hydrogen, lower alkyl, cycloalkyl, aryl ar(lower)alkyl or a group represented by the formula:

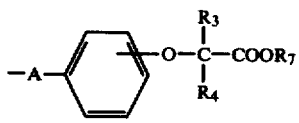

wherein $R_3$, $R_4$, $R_7$ and A are each as defined above, in which the aryl or the ar(lower)alkyl for $R_{1f}$ and $R_{2f}$ may be substituted with halogen, hydroxy or lower alkoxy, and when $R_{1f}$ and $R_{2f}$ are both lower alkyl, $R_{1f}$ and $R_{2f}$ may be linked together;

$R_{2d}$ is hydrogen, lower alkyl, cycloalkyl, aryl or ar(lower)alkyl; in which the aryl or the ar(lower)alkyl for $R_{2d}$ may be substituted with halogen, hydroxy or lower alkoxy, and when $R_{1d}$ and $R_{2d}$ are both lower alkyl, $R_{1d}$ and $R_{2d}$ may be linked together;

$R_8$ is a group convertible into carboxy group;

$R_{1g}$ is lower alkyl, cycloalkyl, aryl, ar(lower)alkyl, a heterocyclic group or a group represented by the formula:

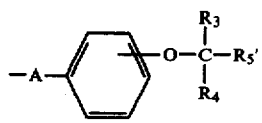

wherein $R_3$, $R_4$, $R_5'$ and A are each as defined above;

$R_{2g}$ is hydrogen, lower alkyl, cycloalkyl, aryl, ar(lower)alkyl, a heterocyclic group or a group represented by the formula:

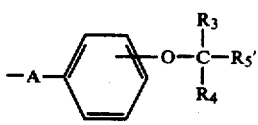

wherein $R_3$, $R_4$, $R_5'$ and A are each as defined above, in which the aryl or the ar(lower)alkyl for $R_{1g}$ and $R_{2g}$ may be substituted with halogen, hydroxy or lower alkoxy, and when $R_{1g}$ and $R_{2g}$ are both lower alkyl, $R_{1g}$ and $R_{2g}$ may be linked together; $R_{1h}$ is lower alkyl, cycloalkyl, aryl, ar(lower)alkyl, a heterocyclic group or a group represented by the formula:

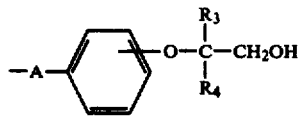

wherein $R_3$, $R_4$ and A are each as defined above;

$R_{2h}$ is hydrogen, lower alkyl, cycloalkyl, aryl, ar(-lower)alkyl, a heterocyclic group or a group represented by the formula:

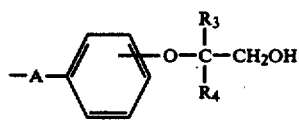

wherein $R_3$, $R_4$ and A are each as defined above, in which the aryl or the ar(lower)alkyl for $R_{1h}$ and $R_{2h}$ may be substituted with halogen, hydroxy or lower alkoxy, and when $R_{1h}$ and $R_{2h}$ are both lower alkyl, $R_{1h}$ and $R_{2h}$ may be linked together;

$R_{1i}$ is lower alkyl, cycloalkyl, aryl, ar(lower)alkyl or a group represented by the formula:

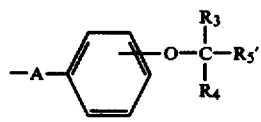

wherein $R_3$, $R_4$, $R_5'$ and A are each as defined above, in which the aryl or the ar(lower)alkyl for $R_{1i}$ may be substituted with halogen or lower alkoxy;

$R_9$ is lower alkyl or ar(lower)alkyl;

$R_6''$ is lower alkoxy;

$R_{1j}$ is lower alkyl, cycloalkyl, aryl or ar(lower)alkyl;

$R_{2j}$ is hydrogen, lower alkyl, cycloalkyl, aryl or ar(-lower)alkyl, in which the aryl or the ar(lower)alkyl for $R_{1j}$ and $R_{2j}$ may be substituted with halogen or hydroxy, and when $R_{1j}$ and $R_{2j}$ are both lower alkyl, $R_{1j}$ and $R_{2j}$ may be linked together; and $R_5''$ is carboxy or esterified carboxy.

(1) Process A: This process comprises reacting a compound (II) or salts thereof with a compound (III) or salts thereof.

Suitable salts of the compound (II) may be alkali metal salt (e.g., sodium salt, potassium salt, etc.), alkaline earth metal salt (e.g., calcium salt, magnesium salt, etc.); a salt with an inorganic acid (e.g., hydrochloric acid, hydrobromic acid, sulfuric acid, etc.); a salt with an organic acid (e.g., acetic acid, maleic acid, fumaric acid, tartaric acid, benzenesulfonic acid, toluenesulfonic acid, etc.) or the like.

The suitable salts of the compound (III) may be aforementioned alkali metal salt, alkaline earth metal salt, a salt with an organic base (e.g., trimethylamine, triethylamine, N,N-dimethylaniline, pyridine, picoline, N,N-dibenzylethylenediamine, etc.) or the like.

The suitable acid residue for Y may be halogen (e.g., chlorine, bromine, fluorine or iodine), alkanesulfonyloxy (e.g., mesyloxy, ethanesulfonyloxy, etc.), arenesulfonyloxy (e.g., benzenesulfonyloxy, tosyloxy, 4-bromobenzenesulfonyloxy, 4-chlorobenzenesulfonyloxy, etc.) or the like.

The present reaction is usually carried out in a solvent such as water, ethanol, acetone, methylisobutylketone, dimethylformamide, ether, benzene or any other solvent which does not give bad influence to the reaction.

The reaction is preferably carried out in the presence of a base such as an inorganic base, for example, alkali metal hydroxide (e.g., sodium hydroxide, potassium hydroxide, etc.), alkaline earth metal hydroxide (e.g., calcium hydroxide, magnesium hydroxide, etc.), alkali metal carbonate (e.g., sodium carbonate, potassium carbonate, etc.), alkaline earth metal carbonate (e.g., calcium carbonate, magnesium carbonate, etc.), alkali metal bicarbonate (e.g., sodium bicarbonate, potassium bicarbonate, etc.) or alkali metal hydride (e.g., sodium hydride, potassium hydride, etc.) or the like, or an organic base, for example, alkali metal alkoxide (e.g., sodium methoxide, sodium ethoxide, etc.), trialkylamine (e.g., trimethylamine, triethylamine, etc.), triethanolamine, N,N-dimethylaniline, N,N-dimethylbenzylamine, N-methylmorpholine, N,N'-dimethylpiperazine, pyridine, quinoline or the like. These bases may be used alone or in combination and a liquid base can serve as a solvent as well.

The reaction temperature is not restrictive and the reaction can be carried out at any temperature of room temperature to under heating.

(2) Process B: This process comprises reacting a compound (IV) with a compound (V) or salts thereof.

The suitable salts of the compound (V) can be also referred to the ones exemplified for the compound (III).

The present reaction is usually carried out in a solvent such as water, ethanol, acetone, ether, dimethylformamide or any other solvent which does not give bad influence to the reaction.

The reaction is preferably carried out in the presence of a base such as an inorganic base, for example, alkali metal hydride (e.g., sodium hydride, potassium hydride, etc.), alkali metal hydroxide (e.g., sodium hydroxide, potassium hydroxide, etc.), alkali metal carbonate (e.g., sodium carbonate, potassium carbonate, etc.), alkali metal bicarbonate (e.g., sodium bicarbonate, potassium bicarbonate, etc.), or an organic base, for example, trialkylamine (e.g., trimethylamine, triethylamine, etc.) or the like. The compound (IV) can serve as a base as well and a liquid base can serve as a solvent as well.

The reaction temperature is not restictive and preferably carried out under cooling or at room temperature.

The starting compound (V) of the present reaction is novel compound and can be prepared by reacting a compound of the formula:

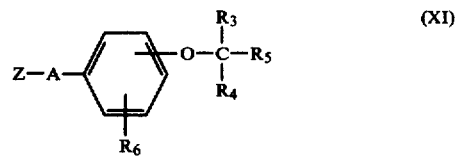

wherein $R_3$, $R_4$, $R_5'$, $R_6$ and A are each as defined above, Z is hydrogen or hydroxy, or salts thereof with a regent which can make Z change into the acid residue.

(3) Process C: This process comprises reducing a compound (VI) or salts thereof.

The suitable salts of the compound (VI) can be also referred to the ones exemplified for the compound (III)

The suitable example of trivalent residue of saturated aliphatic hydrocarbon group for A' may be lower alkylidyne (e.g., methylidyne, ethylidyne, etc.), lower alkanylylidene (e.g., 1-ethanyl-2-ylidene, 1-propanyl-2- ylidene, 1-propanyl-3-ylidene, 2-methyl-1-propanyl-3-ylidene, etc.) or the like.

The suitable example of reduction used in the present reaction is a reduction with a reducing agent such as alkali metal borohydride (e.g., lithium borohydride, sodium borohydride, potassium borohydride, etc.), alkali metal aluminum hydride (e.g., lithium aluminum hydride, etc.), dialkoxyaluminumlithium hydride (e.g., di-tert-butoxyaluminumlithium hydride, dipentyloxyaluminumlithium hydride, etc.), a catalytic reduction or the like.

The suitable catalysts used in the catalytic reduction may be platinum catalyst (e.g., platinum wire, platinum plate, platinum spongy, platinum black, platinum oxide, platinum colloid, etc.), palladium catalyst (e.g., palladium spongy, palladium black, palladium oxide, palladium on barium sulfate, palladium on barium carbonate, palladium on charcoal, palladium on silica gel, palladium colloid, etc.), platinum group metal catalyst (e.g., rhodium on asbestos, iridium, rhodium colloid, luthenium oxide, iridium colloid, etc.), nickel catalyst (e.g., reduced nickel, nickel oxide, Raney nickel, Urushibara nickel, nickel catalyst formed by decomposition of nickel formate, nickel borate, etc.), cobalt catalyst (e.g., reduced cobalt, Raney cobalt, Urushibara cobalt, etc.), iron catalyst (e.g., reduced iron, Raney iron, etc.), copper catalyst (e.g., reduced copper, Raney copper, Ullmann copper etc.), zinc catalyst or the like.

The present reaction can be carried out in any solvent which does not give bad influence to the reaction, and, for example, when the catalytic reduction is employed in the present reaction, the present reaction is preferably carried out in a solvent such as methanol, ethanol, or the like.

The reaction temperature is not restrictive, and the reaction is preferably carried out under cooling or at room temperature.

The starting compound (VI) of the present reaction is novel compound and can be prepared by (a) reacting a compound of the formula:

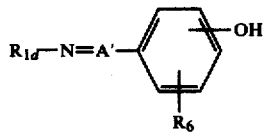
(XII)

wherein $R_{1d}$, $R_6$ and $A'$ are each as defined above, with a compound of the formula:

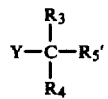
(III)

wherein $R_3$, $R_4$, $R_5'$ and Y are each as defined above or salts thereof, or (b) reacting a compound of the formula:

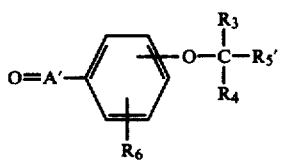
(XIII)

wherein $R_3$, $R_4$, $R_5'$, $R_6$ and $A'$ are each as defined above or salts thereof, with a compound of the formula:

$$R_{1d}-NH_2 \qquad (X)$$

wherein $R_{1d}$ is as defined above.

In the present reaction, when alkali metal aluminum hydride is used as reducing agent, the carboxy or the esterified carboxy group for $R_5'$ is changed into hydroxymethyl group in the course of the reaction, and this is also included in the scope of the present reaction.

(4) Process D: This process comprises (a) reacting a compound ($II_a$) or salts thereof with a compound (VII) in the presence of a strong base, or (b) reacting a compound ($II_a$) or salts thereof with a compound (VIII) and a compound (X) in the presence of a strong base.

The suitable example of halogen for X may be chlorine, bromine, fluorine or iodine.

The suitable salts of the compound ($II_a$) may be alkali metal salt (e.g., sodium salt, potassium salt, etc.), acid salt (e.g., hydrochloride, hydrobromide, etc.) or the like.

The reaction of the process D-a) is carried out by reacting the compound ($II_a$) or salts thereof with the compound (VII) in the presence of a strong base.

The present reaction [process D-a] is carried out in the presence of strong base such as alkali metal hydroxide (e.g., sodium hydroxide, potassium hydroxide, etc.), alkali metal alkoxide, for example, sodium alkoxide (e.g., sodium methoxide, sodium ethoxide, etc.), potassium alkoxide (e.g., potassium methoxide, potassium ethoxide, etc.) or the like.

The present reaction is usually carried out in a solvent such as water, methanol, ethanol, acetone, dioxane, ether, benzene or any other solvent which does not give bad influence to the reaction.

The reaction temperature is not restrictive, and the reaction is preferably carried out at room temperature, under warming or heating. The reaction product is isolated by conventional methods.

The reaction of the process D-b) is carried out by reacting a compound ($II_a$) or salts thereof with a compound (VIII) and a compound (IX) in the presence of a strong base.

The suitable example of strong base can be also referred to the ones exemplified in the process D-a).

The present reaction is usually carried out in a solvent such as water, methanol, ethanol, dioxane, ether, benzene or any other solvent which does not give bad influence to the reaction. And when the starting compound (IX) is in liquid, the compound (IX) can serve as a solvent as well.

The reaction temperature is not restrictive and the reaction is preferably carried out at room temperature, under warming or under heating. The reaction product is isolated by conventional methods.

In the present reaction, the compound (VIII) is firstly reacted with the compound (IX) to give the compound (VII) and then said compound (VII) reacts with compound ($II_a$) to give the object compound ($I_d$).

(5) Process E: This process comprises subjecting a compound ($I_e$) or reactive equivalents thereof to esterification.

The suitable reactive equivalent of the compound ($I_e$) may be salt such as acid salt (e.g., hydrochloride, hydrobromide, sulfuric acid salt, etc.), salt with base, for example, salt with organic base (e.g., trimethylamine salt, triethylamine salt, N,N-dimethylaniline salt, pyridine salt, picoline salt, N,N'-dibenzylethylenediamine salt, etc.), salt with inorganic base (e.g., sodium salt, potassium salt, calcium salt, magnesium salt, etc.), nitrile, acid azide, acid halide, acid anhydride, activated amide, activated ester of the like, and a suitable reactive equivalent can be optionally selected according to the kind of the compound ($I_e$) to be used practically.

The suitable example of lower alkyl for $R_7$ can be also referred to the ones exemplified for the compound (I).

The suitable esterifying agent used in the present reaction may be alcohol of the formula:

$$R_7\text{—OH} \qquad (XIV)$$

wherein $R_7$ is as defined above, or a compound of the formula:

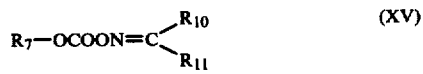

$$R_7\text{—OCOON}=C\begin{array}{c}R_{10}\\R_{11}\end{array} \qquad (XV)$$

wherein $R_7$ is as defined above, $R_{10}$ and $R_{11}$ are each electron withdrawing group.

The suitable electron withdrawing group may be cyano, carbamoyl, lower alkoxycarbonyl (e.g., methoxycarbonyl, ethoxycarbonyl, propoxycarbonyl, butoxycarbonyl, etc.) or the like.

Further lower alkyl halide, di(lower)alkyl sulfate, diazo(lower)alkane, lower alkyl p-toluenesulfonate or the like which has lower alkyl group of $R_7$ as lower alkyl moiety of it can be used as an esterifying agent in the present reaction.

The present reaction is usually carried out in a solvent which does not give bad influence to the reaction. When the alcohol (XIV) is used as an esterifying agent it is convenient to use the alcohol (XIV) serving as a solvent as well.

The reaction temperature is not restrictive and the reaction is preferably carried out at a temperature of room temperature to boiling point of a solvent.

In the present reaction when the compound ($I_e$) is used in a form of free acid, it is preferable to carry out the reaction in the presence of an acid catalyst such as hydrochloric acid, sulfuric acid, boron trifluoride, benzenesulfonic acid, p-toluenesulfonic acid, hydrobromic acid, ferric chloride, aluminum chloride, zinc chloride or the like, or a condensing agent such as N,N'-dicyclohexylcarbodiimide, pentamethyleneketene-N-cyclohexylimine, 1-alkoxy-1-chloroethylene, tetraalkyl pyrophosphite, 2-ethyl-5-(m-sulfophenyl)isoxazolium hydroxide intramolecular salt, 2-ethyl-7-hydroxybenzisoxazolium salt, ethyl polyphosphate, isopropyl polyphosphate, phosphorous oxychloride, phosphorous trichloride, thionyl chloride, oxalyl chloride, 1-(4-chlorobenzenesulfonyloxy)-6-chloro-1H-benzotriazole, strongly acidic ion exchange resin, molecular sieve or the like.

The reaction product is isolated by conventional methods.

The starting compound ($I_g$) is novel compound and can be prepared by some processes mentioned in this specification.

(6) Process F: This process comprises treating a compound ($I_g$) by conventional methods.

The suitable group convertible into carboxy group for $R_8$ includes all groups which can be convertible into carboxy group, the example of which may be ester, acid amide, acid anhydride, nitrile, acid halide, acid azide, or a group formed by reaction of carboxy group with silyl compound [e.g., dimethyldichlorosilane, bis(trimethylsilyl)acetamide, etc.] or nonmetal compound (e.g., titanium tetrachloride, etc.), or the like.

Suitable esters may include, aliphatic esters and esters containing an aromatic or heterocyclic ring. The suitable aliphatic esters may include saturated or unsaturated, lower or higher alkyl esters which may be branched or which may contain a cyclic ring, such as lower or higher aliphatic esters, for example, lower alkyl (e.g., methyl, ethyl, propyl, isopropyl, 1-cyclopropylethyl, butyl, tert-butyl, pentyl, tert-pentyl, hexyl, etc.) esters, lower alkenyl (e.g., vinyl, 1-propenyl, allyl, 1,1-dimethyl-2-propenyl, 3-butenyl, etc.) esters, lower alkynyl (e.g., ethynyl, 1,1-dimethyl-2-propynyl, 3-butynyl, 4-pentynyl, etc.) esters, cycloalkyl (e.g., cyclopentyl, cyclohexyl, cycloheptyl, etc.) esters, etc., and lower or higher aliphatic esters containing a nitrogen, sulfur or oxygen atom, for example, lower alkoxy(lower)alkyl (e.g., methoxymethyl, ethoxyethyl, methoxyethyl, etc) esters, lower alkylthio(lower)alkyl (e.g., methylthiomethyl, methylthioethyl, ethylthioethyl, methylthiopropyl, etc.) esters, di(lower)alkylamino(lower)alkyl (e.g., dimethylaminoethyl, diethylaminoethyl, dipropylaminomethyl, etc.) esters, lower alkylsulfinyl(lower)alkyl (e.g., methylsulfinylmethyl, ethylsulfinylmethyl, etc.) esters, lower alkaneamido(lower)alkyl (e.g., acetoamidomethyl, acetoamidoethyl, etc.) esters, etc.

The suitable esters containing an aromatic ring may include, for example, aryl (e.g., phenyl, xylyl, tolyl, naphthyl, etc.) esters, ar(lower)alkyl (e.g., benzyl, phenethyl, trityl, diphenylmethyl, etc.) esters, aryloxy(lower)alkyl (e.g., phenoxymethyl, phenoxyethyl, phenoxypropyl, etc) esters, arylthio(lower)alkyl (e.g., phenylthiomethyl, phenylthioethyl, phenylthiopropyl, etc.) esters, arylsulfinyl(lower)alkyl (e.g., phenylsulfinylmethyl, phenylsulfinylethyl, etc.) esters, aroyl(lower)alkyl (e.g., benzoylmethyl, toluoylethyl, etc.) esters, etc.

The aliphatic esters and the esters containing an aromatic ring as mentioned above may have 1 to 5 appropriate substituent(s) such as lower alkoxy (e.g., methoxy, ethoxy, propoxy, isopropoxy, butoxy, tertbutoxy, etc.), lower alkanesulfonyl (e.g., mesyl, ethanesulfonyl, etc.), phenylazo, halogen (e.g., chlorine, bromine, fluorine, etc.), cyano, nitro, hydroxy, etc., examples of which are illustrated by mono(or di or tri(halo(lower)alkyl (e.g., chloromethyl, bromoethyl, dichloromethyl, 2,2,2-trichloroethyl, 2,2,2-tribromoethyl, etc.) esters, cyano(lower)alkyl (e.g., cyanomethyl, cyanoethyl, 2-cyano-1,1-dimethylethyl, etc.) esters, mono(or di or tri or tetra or penta)halophenyl (e.g., 4-chlorohenyl, 3,5-dibromophenyl, 2,4,5-trichlorophenyl, 2,4,6-trichlorophenyl, pentachlorophenyl, etc.) esters, lower alkanesulfonylphenyl (e.g., 4-mesylphenyl, 2-ethanesulfonylphenyl, etc.) esters, 2-(or 3- or 4-)phenylazophenyl esters, mono(or di or tri)nitrophenyl (e.g., 4-nitrophenyl, 2,4-dinitrophenyl, 3,4-5-trinitrophenyl, etc.) esters, mono(or di or tri or tetra or penta)halophenyl(lower)alkyl (e.g., 4-chlorobenzyl, 2,4-dibromobenzyl, 3,4,5-trichlorobenzyl, pentachlorobenzyl, etc.) esters, mono(or di or tri)nitrophenyl(lower)alkyl (e.g., 2-nitrobenzyl, 4-nitrobenzyl, 3,4,5-trinitrobenzyl, etc.) esters, mono(or di or tri)(lower)alkoxyphenyl(lower)alkyl (e.g., 4-methoxybenzyl, 3,4-dimethoxybenzyl, 3,4,5-trimethoxybenzyl, etc.) esters, hydroxy and di(lower)alkylphenyl(lower)alkyl (e.g., 3,5-dimethyl-4-hydroxybenzyl, 3,5-ditert-butyl-4-hydroxybenzyl, etc.) esters, mono (or di or tri)nitrophenylthio(lower)alkyl (e.g., 4-nitrophenylthiomethyl, 2,4-dinitrophenylthiomethyl, etc.) esters, mono(or di or tri)halophenylthio(lower)alkyl (e.g., 4-chlorophenylthiomethyl, 3,4,5-trichlorophenylthiomethyl, etc.) esters, mono(or di or tri)nitroaroyl(lower)alkyl (e.g., 4-nitrobenzoylmethyl, 2,4-dinitrobenzoylmethyl, etc.) esters, mono(or di or tri)haloaroyl(lower)alkyl (e.g., 4-chlorobenzoylmethyl, 3,4,5-trichlorobenzoylmethyl, etc.) esters, etc.

And suitable esters may further include esters formed by the reaction of carboxy group with substituted or unsubstituted thioalcohol, N-hydroxysuccinimide, N-hydroxyphthalimide, tetrahydropyranol, 1,3-propanediol, 1-phenyl-3-methyl-5-pyrazolone, 3-hydroxypyridine, 3-hydroxymethylpyridine, 2-hydroxymethylpyridine-1-oxide, 1-hydroxypiperidine, 1-methyl-4-hydroxypiperidine, 1-hydroxy-2(1H)-pyridone, dimethylhydroxylamine, diethylhydroxylamine, glycolamide, 8-hydroxyquinoline, oxime, 2-hydroxymethylquinoline-1-oxide, methoxyacetylene, ethoxyacetylene, N,N-dimethyl-3,3-dimethyl-1-butynylamine, N,N-diethyl-3,3-dimethyl-1-butynylamine, N,N-diethyl-1-butynylamine, 2-ethyl-5-(3-sulfophenyl)isoxazolium hydroxide intramolecular salt, halogeno-9,10-dihydroanthracene (e.g., 1,5,9,9,10-pentachloro-9,10-dihydroanthracene, 9,9,10-trichloro-9,10-dihydranthracene, 1,8,9,10,10-pentachloro-9,10-dihydroanthracene, etc.) or the like.

The suitable acid amides may include, for example, N-lower alkyl acid amide (e.g., N-methyl acid amide, N-ethyl acid amide, etc.), N,N-di(lower)alkyl acid amide (e.g., N,N-dimethyl acid amide, N,N-diethyl acid amide, N-methyl-N-ethyl acid amide, etc.), N-phenyl acid amide, or an acid amide with pyrazole, imidazole, triazol, tetrazol, 4-lower alkylimidazole (e.g., 4-methylimidazole, 4-ethylimidazole, etc.), etc.

The suitable acid anhydrides include, for example, a so-called mixed anhydride with a (lower)alkyl phosphate (e.g., methyl phosphate, ethyl phosphate, etc.), phosphoric acid halide (e.g., phosphoric acid chloride, phosphoric acid bromide, etc.), di(lower)alkyl phosphite (e.g., dimethyl phosphite, diethyl phosphite, etc.), sulfurous acid, thiosulfuric acid, sulfuric acid, lower alkyl carbonate (e.g., methyl carbamate, ethyl carbonate etc.), hydrazoic acid, saturated or unsaturated lower aliphatic carboxylic acid (e.g., pivalic acid,, pentanoic acid, isopentanoic acid, 2-ethylbutanoic acid, crotonic acid, valeric acid, propionic acid, etc.), saturated or unsaturated halo(lower)aliphatic carboxylic acid (e.g., chloroacetic acid, trifluoroacetic acid, 3-chloro-2-pentenoic acid, 3-bromo-2-butenoic acid, etc.), substituted lower aliphatic carboxyic acid (e.g., phenylacetic acid, diphenylacetic acid, phenoxyacetic acid, furanacetic acid, thiopheneacetic acid, etc.), or a symmetric acid anhydride, etc.

As the conventional methods which comprise converting the group R$_8$ of the compound (I$_g$) into a carboxy group to provide the compound (I$_h$), there may be included, for example, reduction, hydrolysis, a method by using anhydrous basic catalyst, etc.

The hydrolysis is carried out by using an acid or a base.

The suitable acid may be an organic acid such as hydrochloric acid, hydrobromic acid, hydrofluoric acid, an organic acid such as formic acid, trihaloacetic acid (e.g., trichloroacetic acid, trifluoroacetic acid, etc.), acetic acid, p-toluenesulfonic acid, trifluoromethanesulfonic acid, a mixture of hydrochloric acid and acetic acid, acidic ion exchange resin or the like. In the hydrolysis using acid, when solvent is used, the reaction is usually carried out in hydrophilic organic solvent, water or a mixture of water and hydrophilic organic solvent.

The suitable base may be inorganic base, for example, alkaline metal hydroxide such as alkali metal hydroxide (e.g., sodium hydroxide, potassium hydroxide, etc.), alkaline earth metal hydroxide (e.g., magnesium hydroxide, calcium hydroxide, etc., alkali metal carbonate, alkaline earth metal carbonate, alkali metal bicarbonate, alkaline earth metal bicarbonate, etc. an organic base such as trialkylamine (e.g., trimethylamine, triethylamine, etc.), picoline, N-methylpyrrolidine, N-methylmorpholine, etc., or basic ion exchange resin, etc. The reaction using base is usually carried out in water, hydrophilic solvent or a mixture thereof.

In case that the group convertible into carboxy group is activated ester, activated amide, acid anhydride, acid halide, acid azide or the like, the hydrolysis reaction is carried out not only under usual conditions, but also milder conditions such as contacting with water.

In case that the group convertible into carboxy group is 2-iodoethyl ester, 2,2,2-trichloroethyl ester, benzyl ester, the reduction is suitably employed in the reaction, and in case that the group convertible into carboxy group is ethynyl ester, 4-hydroxy-3,5-di-tert-butylbenzyl ester or the like, the reduction may be suitably carried out by using a basic catalyst in an anhydrous condition.

The reduction is carried out by using a combination of metal (e.g., zinc, zinc amalgam, tin, etc.) or chrome salt of acid (e.g. chromium chloride, chromium acetate, etc.) and acid (e.g., hydrochloric acid, formic acid, acetic acid, propionic acid, etc.) or by using catalytic reduction or the like.

The suitable catalyst used in the catalytic reduction may be platinum catalyst (e.g., platinum wire, platinum spongy, platinum black, platinum oxide, platinum colloid, etc.), palladium catalyst (e.g., palladium spongy, palladium black, palladium oxide, palladium on barium sulfate, palladium on barium carbonate, palladium on charcoal, palladium on silica gel, palladium colloid, etc.), nickel catalyst (e.g., reduced nickel, nickel oxide, Raney nickel, Urshibara nickel etc.) or the like.

The suitable basic catalyst using in an anhydrous condition may be sodium benzenethiolate, $(CH_3)_2LiCu$ or the like.

The reaction temperature is not restrictive and optionally selected according to the kind of starting compounds (I$_g$), reagents, solvents, etc., to be used.

The starting compound (I$_g$) is novel compound and can be prepared by some processes mentioned in this specification.

(7) Process G: This process comprises reducing a compound (I$_i$).

The present reaction is carried out by reaction with a reducing agent such as alkaline metal aluminum hydride, for example, alkali metal aluminum hydride (e.g., lithium aluminum hydride, sodium aluminum hydride, etc.), alkaline earth metal aluminum hydride (e.g., calcium aluminum hydride, magnesium aluminum hydride, etc.), or by reduction using a combination of an alcohol (e.g., methanol, ethanol, propanol, isopropyl alcohol, butanol, isobutyl alcohol, etc.) and sodium or the like.

The reduction with an alkaline metal aluminum hydride is carried out according to a conventional manner in a solvent such as ether, dibutyl ether, tetrahydrofuran, dioxane or the like.

The reduction with an alcohol and sodium is carried out according to a conventional manner.

The starting compound ($I_l$) is novel compound and can be prepared by some processes mentioned in this specification.

(8) Process H: This process comprises reacting a compound (X) with a compound (V) or salts thereof.

The suitable salts of the compound (V) and reaction conditions are similar to those mentioned in Process B.

In the present reaction, it is preferable to use more than 2 molar equivalents of the compound (V) or salts thereof to the compound (X).

In the present reaction the intermediate of the formula:

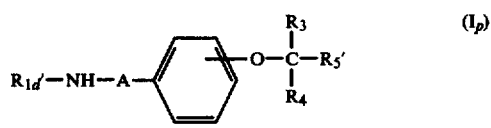

(Ip)

wherein $R_{1d}'$, $R_3$, $R_4$, $R_5'$ and A are each as defined above, may be obtained in the course of the reaction and the compound ($I_p$) can be further reacted with the compound (V) or salts thereof to produce the object compound ($I_k$).

(9) Process I: This process comprises reacting a compound ($I_l$) or salts thereof with a reagent which is able to introduce a substituent into nitrogen atom of the compound ($I_l$).

The suitable salts of the compound ($I_l$) can be also referred to the ones exemplified for the compound (II).

The suitable lower alkyl or ar(lower)alkyl for $R_9$ can be also referred to the ones exemplified for $R_1$ and $R_2$ of the compound (I).

The suitable reagent which is able to introduce a substituent into nitrogen atom which can be used in the present reaction may be a compound of the formula:

$R_9$-Y  (XVI)

wherein $R_9$ and Y are each as defined above; a compound of the formula:

$R_9'$-CHO  (XVII)

wherein $R_9'$ is hydrogen, lower alkyl, aryl or ar(lower)alkyl; di(lower)alkyl sulfate which has lower alkyl group of $R_9$ as lower alkyl moiety thereof, or the like.

More particularly, the reactions as stated above can be explained as follows. That is, the compound ($I_l$) is reacted with the compound (XVI) according to a conventional manner so that the substituent, $R_9$- is introduced to the nitrogen atom thereof to provide the compound ($I_m$) wherein $R_9$ is as defined above. The compound ($I_l$) is reacted with the compound (XVII) under reductive condition according to a conventional manner so that the substituent, $R_9'$—$CH_2$— is introduced to the nitrogen atom to provide the compound ($I_m$) wherein $R_9'$ is as defined above.

And, the compound ($I_l$) is reacted with di(lower)alkyl sulfate according to a conventional manner so that the substituent, lower alkyl is introduced into the nitrogen atom thereof to provide the compound ($I_m$) wherein $R_9$ is lower alkyl.

The starting compound ($I_l$) is novel compound and can be prepared by some processes mentioned in this specification.

(10) Process J: This process comprises subjecting a compound ($I_n$) to dealkylation.

The suitable example of dealkylating agent used in the present reaction may be lower alkanethiol (e.g., methanethiol, ethanethiol, propanethiol, etc.) or alkali metal salts (e.g., sodium salt, potassium salt, etc.) thereof, metal halide (e.g., boron tribromide, boron trichloride, aluminum chloride, aluminum bromide, lithium iodide, etc.) or the like.

The present reaction is usually carried out in a solvent such as dimethylformamide, dimethylsulfoxide, or any other solvent which does not give bad influence to the reaction.

The reaction temperature is not restrictive and the reaction is preferably carried out under warming or heating.

The starting compound ($I_n$) of the present reaction is novel compound and can be prepared by some processes mentioned in this specification.

In the present reaction, when $R_5'$ of the compound ($I_n$) is esterified carboxy, the esterified carboxy group may be changed into carboxy group in the course of the reaction, and this is also included in the scope of the present reaction.

In case that, in the processes B, C, E, F or J mentioned above, are obtained the object compounds having a moiety of the formula:

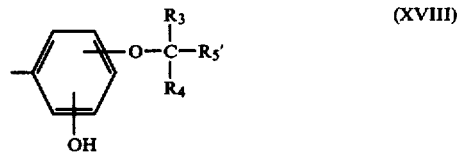

(XVIII)

wherein $R_3$, $R_4$ and $R_5'$ are each as defined above and the hydroxy group is in the ortho position of

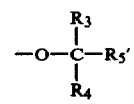

group, these group may be linked together, for example, in courses of conventional posttreatment of the reaction mixtures to form a moiety of the formula:

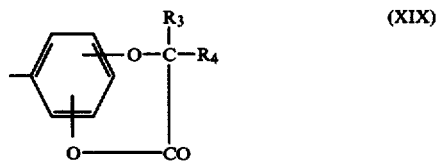

(XIX)

wherein $R_3$ and $R_4$ are each as defined above, and this conversion and the product therein are also included in the scope of the present invention. Thus obtained produced having a moiety of the formula (XIX) also shows a similar pharmacological activity to that of the compound (I). And, in this case, said product may be treated with a base to give salts of a compound having a moiety of the formula:

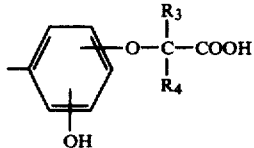

(XX)

wherein $R_3$ and $R_4$ are each as defined above, and this process is also included in the scope of the present invention.

Thus obtained compounds may be converted into pharmaceutically acceptable salt thereof by the conventional methods, if desired.

In this specification, preferable examples of the object compound (I) are illustrated as follows:

preferable example of $R_1$ may be aryl or ar(lower)alkyl;
preferable example of $R_2$ may be hydrogen, lower alkyl, aryl or ar(lower)alkyl; preferable example of $R_3$ may be lower alkyl;
preferable example of $R_4$ may be hydrogen or lower alkyl;
preferable example of $R_5$ may be carboxy or lower alkoxycarbonyl;
preferable example of $R_6$ may be hydrogen, hydroxy or lower alkoxy; and preferable example of A is lower alkylene; in which the aryl or the ar(lower)alkyl for $R_1$ and $R_2$ may be substituted with halogen, hydroxy or lower alkoxy.

The substituted-phenyl substituted-alkyl ethers (I) and pharmaceutically acceptable salts thereof are useful as the therapeutic agents in the treatment of hyperlipemia.

The compounds (I) and pharmaceutically acceptable salts thereof can be administered by the conventional methods, the conventional types of unit dosages or with the conventional pharmaceutical carriers to produce a hypolipidemic activity in human beings. Thus, they can be used in the form of pharmaceutical preparation, which contain them in admixture with a pharmaceutical organic or inorganic carrier material suitable for enteral or parenteral applications. Oral administration by the use of tablets, capsules or in liquid form such as suspensions, solutions or emulsions, or injectional application is particularly advantageous. When formed into tablets, the conventional binding and disintegrating agents used in therapeutic unit dosages can be employed. Illustrative of binding agents there can be mentioned glucose, lactose, gum acacia, gelatin, mannitol, starch paste, magnesium trisilicate and talc. Illustrative of disintegrating agents there can be mentioned corn starch, keratin, colloidal silica and potato starch. When administered as liquids the conventional liquid carriers can be used.

The dosage or therapeutically effective quantity of the compounds (I) and their salts for human beings can vary over wide limits such as that of about 10 to 1000 milligrams/day for adult. The upper limit is limited only by the degree of effect desired and economic considerations. For oral administration it is to employ from about 5 to 30 milligrams of the therapeutic agent per unit dosage. For injectional use, the active ingredient may be employed from 1 to 10 mg per unit dosage. Of course, the dosage of the particular therapeutic agent used can vary considerably, such as the age of the patient and the degree of therapeutic effect desired. By the term pharmaceutical carrier it is intended to include non-therapeutic materials which are conventionally used with unit dosage and includes fillers, diluents, binders, lubricants, disintegrating agents and solvents. Of course, it is possible to administer the novel therapeutics, i.e. the pure compounds, without the use of a pharmaceutical carrier.

Practical and presently-preferred embodiments of this invention are illustratively shown in the following Examples.

EXAMPLE 1 (PROCESS A)

(A) A mixture of 500 mg of 4-(4-chloroanilinomethyl)phenol, 632 mg of ethyl 2-bromo-2-methylpropionate, 7.5 ml of methyl isobutyl ketone and 448 mg of potassium carbonate is refluxed under heating for 6 hours. The insolubles are filtered off from the reaction mixture, and the filtrate is washed with water, dried and concentrated. The residue (730 mg) is purified by column chromatography, using 22 g of silica gel and chloroform as a developer to give 410 mg of ethyl 2-[4-(4-chloroanilinomethyl)phenoxy]-2-methylpropionate, mp 58° to 60° C.

(B) To a solution of 0.256 g of sodium in 30 ml of ethanol is added 2 g of 4-(4-chloroanilinomethyl)-phenol, and 2.02 g of ethyl 2-bromopropionate is further added dropwise at room temperature. The mixture is thereafter refluxed under heating for 5.5 hours. The ethanol is distilled off from the reaction mixture, 20 ml of water is added to the residue, and the diluted residue is extracted with ether. The extract is washed twice with a saturated aqueous solution of sodium chloride and then dried. After distilling off the solvent from the dried extract, the residue (2.9 g) is purified by column chromatography, using 60 g of silica gel and chloroform as a developer, to give 2.1 g of ethyl 2-[4-(4-chloroanilinomethyl)phenoxy]propionate as an oily product.

N.M.R. spectrum (CDCl$_3$, δ)

| ppm | 6.4–7.5 | (8H, m) |
|---|---|---|
| | 4.77 | (1H, q, J = 7Hz) |
| | 4.23 | (2H, q, J = 7Hz) |
| | 4.20 | (2H, s) |
| | 4.1 | (1H, broad s) |
| | 1.57 | (3H, d, J = 7Hz) |
| | 1.22 | (3H, t, J = 7Hz) |

(C) A mixture of 1.9 g of 4-(4-chloroanilinomethyl)-2-methoxyphenol, 2.11 g of ethyl 2-bromo-2-methylpropionate 1.5 g of potassium carbonate and 29 ml of methyl isobutyl ketone is refluxed for 24 hours. To the mixture is further added 705 mg of ethyl 2-bromo-2-methylpropionate and the resulting mixture is further refluxed for 3 hours. The insolubles are filtered off and the filtrate is washed with water, dried and concentrated under reduced pressure. The residual oil is purified by column chromatography, using 60 g of silica gel and benzene as a developer, to give 1.1 g of ethyl 2-[4-(4-chloroanilinomethyl)-2-methoxyphenoxy]-2-methylpropionate, mp 73° to 74° C. Infrared absorption spectrum (nujol) 3400, 1735 cm$^{-1}$. N.M.R.spectrum (CDCl$_3$, δ) ppm 6.45–7.33 (7H, m), 4.25 (2H, q, J=7 Hz), 4.20 (2H, s) 3.79 (3H, s), 1.59 (6H, s), 1.30 (3H, t, J=7 Hz)

(D) The following compounds are obtained by using the similar procedures as those of the above Examples.
(1) Ethyl 2-(4-ethylaminomethylphenoxy)-2-methylpropionate hydrochloride, mp 117° to 119° C.

(2) Ethyl 2-[4-(1-pyrrolidinylmethyl)phenoxy]-2-methylpropionate, colorless oil. Infrared absorption spectrum (liquid film) 1725, 1280, 1230, 1175, 1135, 1020 cm$^{-1}$ (3) Ethyl 2-(4-anilinomethylphenoxy)-2-methylpropionate, mp 45° to 46° C.

(4) Ethyl 2-(4-anilinomethylphenoxy)-2-methylpropionate hydrochloride, mp 158° to 163° C.

(5) Ethyl 2-[4-(p-anisidinomethyl)phenoxy]-2-methylpropionate hydrochloride, mp 119° to 120° C.

(6) Ethyl 2-[4-(4-chloroanilinomethyl)phenoxy]-2-methylpropionate hydrochloride, mp 143° to 145° C.

(7) Ethyl 2-(4-cyclohexylaminomethylphenoxy)-2-methylpropionate hydrochloride, mp 140° to 142° C.

(8) Ethyl 2-(4-isobutylaminomethylphenoxy)-2-methylpropionate hydrochloride, mp 118° to 119° C.

(9) Ethyl 2-(4-benzylaminomethylphenoxy)-2-methylpropionate hydrochloride, mp 138° to 139° C.

(10) Ethyl 2-[4-(p-toluidinomethyl)phenoxy]-2-methylpropionate hydrochloride, mp 133° to 135° C.

(11) Ethyl 2-[4-(3-chloroanilinomethyl)phenoxy]-2-methylpropionate hydrochloride, mp 146° to 148° C.

(12) Ethyl 2-[4-{N-(4-chlorophenyl)-N-methylaminomethyl}phenoxy]-2-methylpropionate, oil. Infrared absorption spectrum (liquid film) 1730, 1280, 1235, 1175, 1140, 1020 cm$^{-1}$.

(13) 2-[4-(4-Chloroanilinomethyl)phenoxy]-2-methylpropionic acid, mp 155° to 158° C.

(14) N,N-bis[4-(1-methyl-1-ethoxycarbonylethoxy)-benzyl]-ethylamine hydrochloride, mp 164° to 165° C.

(15) Ethyl 2-[4-(4-chloroanilinomethyl)phenoxy]-2-methylbutyrate hydrochloride, mp 135° to 137° C.

(16) Ethyl 2-[4-{N-benzyl-N-(4-chlorophenyl)aminomethyl}-phenoxy]-2-methylpropionate hydrochloride, mp 137° to 141° C.

(17) 2-[4-(4-Chloroanilinomethyl)phenoxy]propionic acid, mp 148° to 149° C.

(18) 2-[4-(4-Chloroanilinomethyl)phenoxy]-2-methylbutyric acid, mp 152° to 153° C.

(19) 2-[4-{N-Methyl-N-(4-chlorophenyl)aminomethyl}phenoxy]-2-methylpropionic acid, mp 63° to 65° C.

(20) 2-[4-{N-Benzyl-N-(4-chlorophenyl)aminomethyl}phenoxy]-2-methylpropionic acid, mp 65° to 67° C.

(21) Ethyl 2-[4-(2-benzothiazolylaminomethyl)phenoxy]-2-methylpropionate hydrochloride, mp 219° to 220° C.

(22) Ethyl 2-[4-(2-pyridylaminomethyl)phenoxy]-2-methyl-propionate, mp 78° to 79° C.

EXAMPLE 2 (PROCESS B)

(A) (a) A mixture of 20 g of ethyl 2-(p-tolyloxy)-2-methylpropionate, 17.7 g of N-bromosuccinimide, 0.2 g of benzoyl peroxide and 140 ml of anhydrous carbon tetrachloride is refluxed under heating for 4 hours. After the reaction, the reaction mixture is left to stand for cooling and washed with water. The carbon tetrachloride layer is dried and then concentrated. The resulting oily product (28 g) is distilled under reduced pressure to give 18.3 g of ethyl 2-(4-bromomethylphenoxy)-2-methylpropionate, bp 146° to 148° C./1-2 mmHg.

(b) 50 ml of 40% ethanol solution of ethylamine and 4.58 g of potassium carbonate are suspended in 50 ml of absolute ethanol. Over a period of 1.25 hours, a solution of 10 g of ethyl 2-(4-bromomethylphenoxy)-2-methylpropionate in 20 ml of absolute ethanol is added dropwise to the suspension with ice-cooling and stirring, and the mixture is stirred for 1 day while being cooled with water. After the reaction, the ethanol is distilled off, water is added to the residue and the diluted residue is extracted three times with benzene. The extract is washed twice with a saturated aqueous solution of sodium chloride and dried over magnesium sulfate, and the solvent is distilled off. The resulting 8.87 g of pale yellow oil is subjected to column chromatography with 88 g of silica gel, using 2% methanol-benzene solution first and then 5% methanol-benzene solution for elution. The solvent is distilled off from the 5% methanol-benzene eluate to give 3.93 g of an oil product, which is then converted to its hydrochloride by using a mixture of hydrochloric acid and ethanol, namely 4.14 g of ethyl 2-(4-ethylaminomethylphenoxy)-2-methylpropionate hydrochloride, mp 117° to 119° C.

(B) To 15 ml of pyrrolidine being ice-cooled and stirred is added dropwise 5.0 g of ethyl 2-(4-bromomethylphenoxy)-2-methylpropionate prepared in the similar manner as in Example 2 (A) (a), and the mixture is thereafter stirred at room temperature for 30 minutes. An aqueous solution of sodium bicarbonate and ether are added to the reaction mixture for extraction, and the extract is thoroughly washed with water seven to eight times and further extracted twice with dilute hydrochloric acid. The dilute hydrochloric acid extract is washed with ether three times and thereafter basified with an aqueous solution of sodium bicarbonate. The resulting extract is further extracted twice with ether, and the extract is washed with water twice and then dried over magnesium sulfate. The solvent is distilled off from the extract to give 2.9 g of an oily product, which is then caused to be adsorbed by 15 g of alumina and is thereafter eluted with benzene. The solvent is distilled off from the eluate under highly reduced pressure to give 2.63 g of ethyl 2-[4-(1-pyrrolidinylmethyl)-phenoxy]-2-methylpropionate as a colorless oil. Infrared absorption spectrum (liquid film) 1725, 1280, 1230, 1175, 1135, 1020 cm$^{-1}$.

(C) 4.98 g of 2-benzothiazolamine is dissolved in 49 ml of dimethylformamide, and 1.76 g of 50% sodium hydride is gradually added to the solution with ice-cooling and stirring. The mixture is stirred at the same temperature for 1.5 hours. To the resulting solution is added dropwise, with ice-cooling and stirring, a solution of 10.0 g of ethyl 2-(4-bromomethylphenoxy)-2-methylpropionate in 10 ml of dimethylformamide. The mixture is stirred at the same temperature for 1.5 hours. To the reaction mixture are added 30 ml of methanol and then water, and the mixture is extracted four times with ether. The extract is washed with water four times and then dried over magnesium sulfate. The solvent is distilled off, and the resulting 10.84 g of oily product is purified by column chromatography, using 100 g of silica gel and 2% methanol-benzene solution as a developer, to give 3.92 g of an oily product. In conventional manner, the oily product is converted, with a hydrochloric acid-ethanol solution, to its hydrochloride, i.e. 2.04 g of ethyl 2-[4-(2-benzothiazolylaminomethyl)-phenoxy]-2-methylpropionate hydrochloride, mp 193° to 198° C. The crystals are recrystallized from 24 ml of ethanol and collected by filtration to give 1.3 g of a pure product, mp 219° to 220° C. On the other hand, the solvent is distilled off from the filtrate. Recrystallization of the residue from 5 ml of ethanol, followed by treatment with activated carbon, gives 0.2 g of a pure product similarly melting at 219° to 220° C.

(D) In 62 ml of dimethylformamide are suspended 6.25 g of 2-pyridinamine and 9.18 g of powdery potassium carbonate. Over a period of 30 minutes, a solution of 20.0 g of ethyl 2-(4-bromomethylphenoxy)-2-methylpropionate in 20 ml of dimethylformamide is added dropwise to the suspension with ice-cooling and stirring. The mixture is stirred at the same temperature for 2 hours. Water is added to the reaction mixture, and the resulting mixture is extracted three times with ether. The extract is washed with water and is further subjected to extraction three times with dilute hydrochloric acid. The dilute hydrochloric acid layer is washed with ether, then basified with sodium carbonate and extracted three times with ether. The extract is washed with water twice, thereafter dried over magnesium sulfate and the solvent is distilled off. The resulting 10 g of orange oil is purified by column chromatography with 100 g of silica gel, using chloroform first and then 3% methanol-chloroform as developers, to give 2.3 g of an oily product. After addition of 3 ml of ether and n-hexane to the oily product, the product is pulverized and then collected by filtration to give 1.52 g of ethyl 2-[4-(2-pyridylaminomethyl)phenoxy]-2-methylpropionate, mp 78° to 79° C. An additional 0.07 g of the product is obtained from the mother liquor. Total yield: 1.59 g.

(E) The following compounds are obtained by using the similar procedures as those of the Examples 2 (A) to 2 (D).
(1) Ethyl 2-(4-anilinomethylphenoxy)-2-methylpropionate, mp 45° to 46° C.
(2) Ethyl 2-(4-anilinomethylphenoxy)-2-methylpropionate hydrochloride, mp 158° to 163° C.
(3) Ethyl 2-[4-(p-anisidinomethyl)phenoxy]-2-methylpropionate hydrochloride, mp 119° to 120° C.
(4) Ethyl 2-[4-(4-chloroanilinomethyl)phenoxy]-2-methylpropionate hydrochloride, mp 143° to 145° C.
(5) Ethyl 2-[4-(4-chloroanilinomethyl)phenoxy]-2-methylpropionate, oil.
(6) Ethyl 2-(4-cyclohexylaminomethylphenoxy)-2-methylpropionate hydrochloride, mp 140° to 142° C.
(7) Ethyl 2-(4-isobutylaminomethylphenoxy)-2-methylpropionate hydrochloride, mp 118° to 119° C.
(8) Ethyl 2-(4-benzylaminomethylphenoxy)-2-methylpropionate hydrochloride, mp 138° to 139° C.
(9) Ethyl 2-[4-(p-toluidinomethyl)phenoxy]-2-methylpropionate hydrochloride, mp 133° to 135° C.
(10) Ethyl 2-[4-(3-chloroanilinomethyl)phenoxy]-2-methylpropionate hydrochloride, mp 146° to 148° C.
(11) Ethyl 2-[4-{N-(4-chlorophenyl)-N-methylaminomethyl}-phenoxy]-2-methylpropionate, oil. Infrared absorption spectrum (liquid film) 1730, 1280, 1235, 1175, 1140, 1020 cm⁻¹.
(12) 2-[4-(4-Chloroanilinomethyl)phenoxy]-2-methylpropionic acid, mp 155° to 158° C.
(13) Ethyl 2-[4-(4-chloroanilinomethyl)phenoxy]-2-methylbutyrate hydrochloride, mp 135° to 137° C.
(14) 2-[2-[4-(4-Chloroanilinomethyl)phenoxy]-2-methylbutyric acid, mp 152° to 153° C.
(15) Ethyl 2-[4-(4-chloroanilinomethyl)phenoxy]propionate, oil. Infrared absorption spectrum (liquid film) 3410, 1740 cm⁻¹.
N.M.R. spectrum (CDCl₃, δ)

| ppm | |
|---|---|
| 6.3–7.3 | (8H, m) |
| 4.65 | (1H, q, J = 7Hz) |
| 4.15 | (2H, q, J = 7Hz) |
| 4.13 | (2H, s) |
| 3.6–4.0 | (1H, broad s) |
| 1.55 | (3H, d, J = 7Hz) |
| 1.20 | (3H, t, J = 7Hz) |

(16) 2-[4-(4-Chloroanilinomethyl)phenoxy]propionic acid, mp 148° to 149° C.
(17) Ethyl 2-[4-{N-(4-chlorophenyl)-N-benzylaminomethyl}-phenoxy]-2-methylpropionate hydrochloride, mp 137° to 141° C.
(18) 2-[4-{N-(4-Chlorophenyl)-N-benzylaminomethyl}-phenoxy]-2-methylpropionic acid, mp 65° to 67° C.
(19) 2-[4-{N-(4-Chlorophenyl)-N-methylaminomethyl}phenoxy]-2-methylpropionic acid, mp 63° to 65° C.
(20) Ethyl 2-[4-(4-chloroanilinomethyl)-2-methoxyphenoxy]-2-methylpropionate, mp 73° to 74° C.
(21) Sodium 2-[4-(4-chloroanilinomethyl)-2-hydroxyphenoxy]-2-methylpropionate, mp 121° to 125° C.
(22) 3,3-Dimethyl-7-(4-chloroanilinomethyl)-1,4-benzodioxan-2-one, mp 97° to 98° C.

EXAMPLE 3 (PROCESS C)

(A) (a) To 170 ml of absolute ethanol is added 1.48 g of sodium, and 8.4 g of 4-(N-phenylformimidoyl)phenol is added to the mixture at room temperature with stirring to prepare a solution. 12.5 g of ethyl 2-bromo-2-methylpropionate is added to the solution, and the mixture is refluxed under heating for 5 hours. After the reaction, the ethanol is distilled off. The residue is dissolved in ether and thereafter washed with 5% aqueous solution of sodium hydroxide and then with water. After drying the resulting mixture, the ether is distilled off to give 9.2 g of ethyl 2-[4-(N-phenylformimidoyl)-phenoxy]-2-methylpropionate. Infrared absorption spectrum (liquid film) 1735, 1280, 1245, 1170, 1140, 1020 cm⁻¹.

(b) In 90 ml of methanol is dissolved 9.0 g of ethyl 2-[4-(N-phenylformimidoyl)phenoxy]-2-methylpropionate. Over a period of 1.5 hours, 1.1 g of sodium borohydride is added to the solution at 15° to 20° C. with cooling and stirring, and the mixture is stirred at room temperature for 1 hour. After the reaction, the methanol is distilled off under reduced pressure, the residue is dissolved in ether, and the ethereal solution is washed with water and dried. Removal of the ether by distillation gives an oily residue (7.7 g), which partially solidifies when left to stand. The residue is washed with a mixture of benzene and petroleum ether, and the crystals are collected by filtration to give 1.2 g of ethyl 2-(4-anilinomethylphenoxy)-2-methylpropionate, mp 45° to 46° C. The filtrate is concentrated, and the residue is dissolved in ether. Addition of a mixture of hydrochloric acid and ethanol to the solution yields crystals, which are collected by filtration and washed with ether to give 5.2 g of ethyl 2-(4-anilinomethylphenoxy)-2-methylpropionate hydrochloride, mp 158° to 163° C. The product is recrystallized twice from isopropanol to give 3.9 g of a pure product, mp 167° to 168° C.

Elementary analysis: C₁₉H₂₃NO₃·HCl Calcd. C 65.23; H 6.91; N 3.89. Found C 65.05; H 6.90; N 3.90.

(B) (a) 2.38 g of 50% sodium hydride is suspended in 75 ml of anhydrous dimethylformamide, and 7.5 g of 4-[N-(4-methoxyphenyl)formimidoyl]phenol is added in four portions to the suspension at room temperature with stirring. Subsequently, 9.65 g of ethyl 2-bromo-2- methylpropionate is added dropwise to the resulting mixture at 20° to 25° C. over a period of about 40 minutes. The mixture is stirred at room temperature for 1 hour and then at 50° to 55° C. for 2 hours. The reaction mixture is poured into cold water, extracted with ether, and the extract is washed with 5% aqueous solution of sodium hydroxide until disappearance of the color of the aqueous layer, then washed with water and dried. After drying, the ether is distilled off to give 7.5 g of ethyl 2-[4-{N-(4-methoxyphenyl)formimidoyl}phenoxy]-2-methylpropionate in the form of an oil.

Infrared absorption spectrum (liquid film) 1735, 1285, 1245, 1170, 1140, 1020 cm$^{-1}$.

(b) In 75 ml of methanol is dissolved 7.5 g of ethyl 2-[4-{N-(4-methoxyphenyl)formimidoyl}phenoxy]-2-methylpropionate. Over a period of 1.5 hours, 0.84 g of sodium borohydride is added to the solution at 15° to 20° C. with cooling and stirring. After stirring the mixture at room temperature for 1 hour, the methanol is distilled off, and the residue is dissolved in ether. The ethereal solution was washed with water and dried. The ether is distilled off, and the resulting oily residue (6.3 g) is dissolved in 50 ml of ether. A mixture of hydrochloric acid and ethanol is added in excess to the solution. The ether is removed from the resulting mixture until crystals start to precipitate out. The mixture is left to stand with cooling, and the crystalline precipitate is collected by filtration to give 4.9 g of ethyl 2-[4-(p-anisidinomethyl)phenoxy]-2-methylpropionate hydrochloride. The product is recrystallized twice from a mixture of isopropanol and isopropyl ether to give 3.6 g of a pure product, mp 119° to 120° C.

Elementary analysis: $C_{20}H_{25}NO_4 \cdot HCl$ Calcd. C 63.23; H 6.90; N 3.69. Found C 63.49; H 7.10; N 3.64.

(C) (a) 0.312 g of 50% sodium hydride is suspended in 10 ml of anhydrous dimethylformamide, and 1.16 g of 4-[N-(4-chlorophenyl)formimidoyl]phenol is added to the suspension at 20° to 25° C. with stirring. Subsequently over a period of 15 minutes, 1.27 g of ethyl 2-bromo-2-methylpropionate is added dropwise to the resulting mixture at the same temperature with stirring. The mixture is stirred at the same temperature for 30 minutes, then at 50° to 55° C. for 2 hours and thereafter at 80° C. for 3 hours. The reaction mixture is poured into cold water, extracted with ether, and the extract is washed with 5% aqueous solution of sodium hydroxide and then with water. After drying, the solvent is distilled off to give 1.5 g of ethyl 2-[4-{N-(4-chlorophenyl)formimidoyl}phenoxy]-2-methylpropionate.

Infrared absorption spectrum (liquid film) 1735, 1280, 1245, 1170, 1140, 1020 cm$^{-1}$.

(b) In 40 ml of methanol is dissolved 5.3 g of ethyl 2-[4-{N-(4-chlorophenyl)formimidoyl}phenoxy]-2-methylpropionate. Over a period of about 1 hour, 0.58 g of sodium borohydride is added to the solution at 20° to 25° C. with stirring. After stirring the mixture at room temperature for 1 hour, the methanol is distilled off, and the residual oil is dissolved in ether. The solution is washed with water and dried, and the ether is thereafter distilled off. The resulting oily residue (4.2 g) is dissolved in 20 ml of ether. A mixture of hydrochloric acid and ethanol is added to the solution. The resulting precipitate is collected by filtration and washed with ether to give 3.9 g of ethyl 2-[4-(4-chloroanilinomethyl)phenoxy]-2-methylpropionate hydrochloride, mp 139° to 141° C. Recrystallization of the crystals from a mixture of methanol and ether gives 3.1 g of crystals, mp 143° to 145° C. The crystals are suspended in a mixture of ether and water, and the suspension is adjusted to pH 8 to 9 by addition of 28% ammonia water. The ether layer is thereafter separated, washed with water and dried. After drying, removal of the ether by distillation gives 2.9 g of ethyl 2-[4-(4-chloroanilinomethyl)phenoxy]-2-methylpropionate as an oil.

(D) (a) To 70 ml of absolute ethanol is added 872 mg of sodium, and 7 g of 4-(N-cyclohexylformimidoyl)phenol is added to the solution. Subsequently, 7.4 g of ethyl 2-bromo-2-methylpropionate is further added. The mixture is refluxed under heating and with stirring for 15 hours. After distilling off the ethanol from the reaction mixture, water is added to the residue, and the solution is extracted three times with benzene. The extract is washed with water twice, with cooled dilute aqueous solution of sodium hydroxide three times and then with water twice. After drying the resulting solution over magnesium sulfate, the solvent is distilled off to give 5.54 g of ethyl 2-[4-(N-cyclohexylformimidoyl)phenoxy]-2-methylpropionate as an oil.

Infrared absorption spectrum (liquid film) 1740, 1280, 1235, 1170, 1020 cm$^{-1}$.

(b) In 50 ml of methanol is dissolved 5.54 g of ethyl 2-[4-(N-cyclohexylformimidoyl)phenoxy]-2-methylpropionate, and 0.5 g of sodium borohydride is gradually added to the solution with stirring and cooling with water. The mixture is stirred at the same temperature for 1 hour. After the reaction, the methanol is distilled off, water is added to the residue, and the solution is extracted twice with benzene. The extract is washed with water, then with cooled dilute aqueous solution of sodium hydroxide and thereafter with water, twice respectively. After drying the extract over magnesium sulfate, the solvent is distilled off. The resulting oily product (6.0 g) is purified by column chromatography with 60 g of silica gel, using chloroform first and then a mixture of 100 ml of chloroform and 5 ml of methanol as developers. 4.67 g of the resulting oily product is then dissolved in ether. A mixture of hydrochloric acid and ethanol is added to the solution, and the resultant precipitate is collected by filtration to give 4.6 g of ethyl 2-(4-cyclohexylaminomethylphenoxy)-2-methylpropionate hydrochloride, mp 140° to 142° C. Recrystallization of the crystals from a mixture of 5 ml of isopropanol and 80 ml of ether gives 4.0 g of colorless needles, mp 140° to 142° C.

(E) (a) To 100 ml of absolute ethanol is added 0.80 g of sodium, and 5.5 g of 4-(N-isobutylformimidoyl)phenol is added to the solution. Subsequently, 6.78 g of ethyl 2-bromo-2-methylpropionate is further added. The mixture is refluxed under heating and with stirring for 10 hours. After distilling off the ethanol from the reaction mixture, water is added to the residue, which is then extracted three times with benzene. The extract is washed with water twice and dried, and the solvent is removed therefrom to give 5.61 g of ethyl 2-[4-(N-isobutylformimidoyl)phenoxy]-2-methylpropionate in the form of a pale orange oil.

Infrared absorption spectrum (liquid film) 1741, 1650 cm$^{-1}$.

(b) In 56 ml of methanol is dissolved 5.61 g of ethyl 2-[4-(N-isobutylformimidoyl)phenoxy]-2-methylpropionate, and 0.6 g of sodium borohydride is gradually added to the solution with stirring and cooling with water. After the reaction, the methanol is distilled off under reduced pressure, water is added to the residue, and the diluted residue is extracted three times with benzene. The extract is washed with water twice, then with cooled dilute aqueous solution of sodium hydroxide three times and thereafter with water twice. After drying the resulting solution over magnesium sulfate, the solvent is distilled off. The resulting oily product (4.25 g) is dissolved in ether. Addition of a mixture of hydrochloric acid and ethanol to the ethereal solution produces crystals, which are collected by filtration and washed with ether to give 3.6 g of ethyl 2-(4-isobutylaminomethylphenoxy)-2-methylpropionate hydrochloride, mp 115° to 117° C. The product is recrystallized from a mixture of isopropanol and ether to give 2.3 g of a purified product, mp 118° to 119° C.

(F) (a) To 50 ml of absolute ethanol is added 0.573 g of sodium, and 5 g of 4-(N-benzylformimidoyl)phenol and then 5.54 g of ethyl 2-bromo-2-methylpropionate are added to the solution under cooling with water. The mixture is refluxed under heating and with stirring for 22 hours. The ethanol is distilled off from the reaction mixture under reduced pressure. After dissolving the residue in 30 ml of benzene, the insolubles are filtered off. The benzene filtrate is washed with water twice, then dried over magnesium sulfate and thereafter the solvent is distilled off. 6.12 g of the resulting oily product is dissolved in ether. After removing the insolubles from the ethereal solution by filtration, the filtrate is concentrated to give 5.06 g of ethyl 2-[4-(N-benzylformimidoyl)phenoxy]-2-methylpropionate in the form of a pale brown oil.

Infrared absorption spectrum (liquid film) 1740, 1285, 1240, 1175, 1140 cm$^{-1}$.

(b) In 90 ml of methanol is dissolved 4.76 g of ethyl 2-[4-(N-benzylformimidoyl)phenoxy]-2-methylpropionate, and 0.4 g of sodium borohydride is gradually added to the solution with stirring and cooling with water. After the reaction, the methanol is distilled off under reduced pressure, water is added to the residue, and the diluted residue is extracted three times with ether. The extract is washed with water twice, then with ice-cooled dilute aqueous solution of sodium hydroxide three times and thereafter with water twice. After drying the resulting solution over magnesium sulfate, the solvent is distilled off. The resulting pale yellow oily product (4.12 g) is dissolved in ether. Addition of a mixture of hydrochloric acid and ethanol to the ethereal solution with cooling produces crystals, which are collected by filtration and washed with ether to give 4.14 g of ethyl 2-(4-benzylaminomethylphenoxy)-2-methylpropionate hydrochloride, mp 136° to 138° C. The crystals are dissolved in 20 ml of isopropanol, and the solution is treated with activated carbon. Addition of 50 ml of ether to the resulting solution gives 2.9 g of colorless needles, mp 138° to 139° C.

(G) (a) To 50 ml of absolute ethanol is added 0.58 g of sodium, and 4.2 g of 4-[N-(p-tolyl)formimidoyl]phenol and then 7.84 g of ethyl 2-bromo-2-methylpropionate are added to the solution at room temperature with stirring. The mixture is refluxed under heating and with stirring for 5 hours on an oil bath. After distilling off the ethanol from the reaction mixture, the residue is dissolved in ether. The solution is washed with 5% aqueous solution of sodium hydroxide and then with water. After drying the solution, the ether is distilled off, and the residue is further concentrated under reduced pressure on an oil bath at 100° C. to give 4.0 g of ethyl 2-[4-{N-(p-tolyl)formimidoyl}phenoxy]-2-methylpropionate as an oily product.

Infrared absorption spectrum (liquid film) 1735, 1285, 1240, 1160, 1140, 1020 cm$^{-1}$.

(b) In 36 ml of methanol is dissolved 3.6 g of ethyl 2-[4-{N-(p-tolyl)formimidoyl}phenoxy]-2-methylpropionate. Over a period of 40 minutes, 0.42 g of sodium borohydride is added to the solution at 15° to 20° C. with cooling and stirring, and the mixture is stirred at the same temperature for 1 hour. After the reaction, the methanol is distilled off, and the residue is dissolved in ether. The solution is washed with water and dried. After drying, the ether is distilled off. The resulting oily residue (3.4 g) is dissolved in 30 ml of ether. A mixture of hydrochloric acid and ethanol is added dropwise to the solution with cooling. The precipitated crystals are collected by filtration and washed with ether to give 2.6 g of ethyl 2-[4-(p-toluidinomethyl)phenoxy]-2-methylpropionate hydrochloride, mp 126° to 130° C. Recrystallization of the crystals from a mixture of ethanol and isopropyl ether gives 1.7 g of crystals, mp 133° to 135° C.

(H) (a) To 60 ml of absolute ethanol is added 0.58 g of sodium, and 4.6 g of 4-[N-(3-chlorophenyl)formimidoyl]phenol and then 5.84 g of ethyl 2-bromo-2-methylpropionate are added to the solution at room temperature with stirring. The mixture is refluxed under heating and with stirring for 5 hours. After distilling off the ethanol from the reaction mixture, the residue is dissolved in ether. The solution is washed with 5% aqueous solution of sodium hydroxide until disappearance of the color of the aqueous layer, then washed with water and dried. After drying, the solvent is distilled off to give 4.1 g of ethyl 2-[4-{N-(3-chlorophenyl)formimidoyl}phenoxy]-2-methylpropionate.

Infrared absorption spectrum (liquid film) 1730, 1300, 1280, 1240, 1160, 1140, 1020 cm$^{-1}$.

(b) In 40 ml of methanol is dissolved 4.0 g of ethyl 2-[4-{N-(3-chlorophenyl)formimidoyl}phenoxy]-2-methylpropionate. Over a period of 1 hour, 0.44 g of sodium borohydride is added to the solution at 15° to 20° C. with cooling and stirring, and the mixture is stirred at the same temperature for 1 hour. After the reaction, the methanol is distilled off, and the residue is dissolved in ether. The solution is washed with water and dried. After drying, the ether is distilled off, and the resulting oily residue (3.8 g) is dissolved in 30 ml of ether. A mixture of hydrochloric acid and ethanol is added to the solution, and the resulting mixture is left to stand. The precipitated crystals are filtered off and washed with ether to give 3.0 g of ethyl 2-[4-(3-chloroanilinomethyl)phenoxy]-2-methylpropionate hydrochloride, mp 138° to 142° C. Recrystallization of the crystals from a mixture of ethanol and ether gives 1.6 g of crystals, mp 146° to 148° C.

(I) In 50 ml of ethanol is dissolved 33.15 g of ethyl 2-[4-{N-(4-chlorophenyl)formimidoyl}phenoxy]propionate prepared from 4-[N-(4-chlorophenyl)formimidoyl]phenol and ethyl 2-bromopropionate by using the similar manner as that of Example 3 (C) (a). With ice-cooling and stirring, the ethanol solution is added dropwise to a solution prepared by adding 3.79 g of sodium borohydride to 150 ml of ethanol with stirring. The mixture is thereafter stirred at room temperature for 1 hour. The reaction mixture is poured into 1.5 l of water and then extracted with ether. The extract is washed with water and dried over magnesium sulfate. After drying, the solvent is distilled off, and the resulting oily residue (32.50 g) is subjected to silica gel column chromatography for purification, using benzene as a developer. This gives 13.5 g of ethyl 2-[4-(4-chloroanilinomethyl)phenoxy]propionate.

Infrared absorption spectrum (liquid film) 3410, 1740 cm$^{-1}$. N.M.R. spectrum (CDCl$_3$,δ)

| ppm | 6.3–7.3 | (8H, m) |
|---|---|---|
| | 4.65 | (1H, q, J = 7Hz) |
| | 4.15 | (2H, q, J = 7Hz) |
| | 4.13 | (2H, s) |
| | 3.6–4.0 | (1H, broad s) |
| | 1.55 | (3H, d, J = 7Hz) |
| | 1.20 | (3H, t, J = 7Hz) |

(J) In 600 ml of methanol is dissolved 20 g of ethyl 2-(4-formylphenoxy)-2-methylpropionate, and 10.8 g of 4-chloroaniline is added to the solution. The mixture is stirred at 50° C. for 5 hours. Subsequently, 3.2 g of sodium borohydride is added at room temperature to the resulting solution containing ethyl 2-[4-{N-(4-chlorophenyl)formimidoyl}phenoxy]-2-methylpropionate. The mixture is stirred for 1.5 hours. The reaction mixture is concentrated, and water is added to the residue. The diluted residue is extracted with ethyl acetate, and the extract is washed with water and dried. Distillation of the dried extract to remove the solvent gives an oily product (22 g), 2 g of which is subjected to column chromatography with 60 g of silica gel, using chloroform as a developer, to give 1.12 g of ethyl 2-[4-(4-chloroanilinomethyl)phenoxy]-2-methylpropionate, mp 58° to 60° C. 1.12 g of the crystals are dissolved in 20 ml of ether, and a mixture of hydrochloric acid and ethanol is added to the solution. The resulting precipitate is collected by filtration and washed with ether to give 1.05 g of ethyl 2-[4-(4-chloroanilinomethyl)phenoxy]-2-methylpropionate hydrochloride, mp 139° to 141° C. The crystals are recrystallized from a methanol-ether mixture to obtain a purified product, mp 143° to 145° C.

(K) (a) In 100 ml of dried benzene are dissolved 17.0 g of ethyl 2-(4-formylphenoxy)propionate and 9.73 g of 4-chloroaniline, and the mixture is refluxed under heating and with stirring for 6 hours. Concentration of the reaction mixture gives 24.0 g of ethyl 2-[4-{N-(4-chlorophenyl)formimidoyl}phenoxy]propionate as an oily product.

Infrared absorption spectrum (liquid film) 1750, 1630, 1605 cm$^{-1}$.

N.M.R. spectrum (CDCl$_3$,δ)

| ppm | 8.32 | (1H, s) |
|---|---|---|
| | 6.7–8.0 | (8H, m) |
| | 4.82 | (1H, q, J = 7Hz) |
| | 4.22 | (2H, q, J = 7Hz) |
| | 1.65 | (3H, d, J = 7Hz) |
| | 1.27 | (3H, t, J = 7Hz) |

(b) 1.9 g of sodium borohydride is added to 75 ml of ethanol with stirring, and to the solution is added dropwise, with cooling with water, a solution of 16.58 g of ethyl 2-[4-{N-(4-chlorophenyl)formimidoyl}phenoxy]propionate in 25 ml of ethanol. The mixture is then stirred at room temperature for 2 hours. The reaction mixture is poured into 0.75 l of water and is extracted with ether. The extract is washed with water and then dried over magnesium sulfate. Removal of the solvent by distillation gives a pale yellow residual oil (16.25 g), which is purified by column chromatography with silica gel, using benzene as a developer to give 6.75 g of ethyl 2-[4-(4-chloroanilinomethyl)phenoxy]propionate as an oily product.

Infrared absorption spectrum (liquid film) 3410, 1740 cm$^{-1}$.

N.M.R. spectrum (CDCl$_3$,δ)

| ppm | 6.3–7.3 | (8H, m) |
|---|---|---|
| | 4.65 | (1H, q, J = 7Hz) |
| | 4.15 | (2H, q, J = 7Hz) |
| | 4.13 | (2H, s) |
| | 3.6–4.0 | (1H, broad s) |
| | 1.55 | (3H, d, J = 7Hz) |
| | 1.20 | (3H, t, J = 7Hz) |

(L) The following compounds are obtained by using the similar procedures as those of the Examples 3 (A) to 3 (K).

(1) Ethyl 2-(4-ethylaminomethylphenoxy)-2-methylpropionate hydrochloride, mp 117° to 118° C.

(2) 2-[4-(4-Chloroanilinomethyl)phenoxy]-2-methylpropionic acid, mp 155° to 158° C.

(3) Ethyl 2-[4-(4-chloroanilinomethyl)phenoxy]-2-methylbutyrate hydrochloride, mp 135° to 137° C.

(4) 2-[4-(4-Chloroanilinomethyl)phenoxy]-2-methylbutyric acid, mp 152° to 153° C.

(5) 2-[4-(4-Chloroanilinomethyl)phenoxy]propionic acid, mp 148° to 149° C.

(6) 2-[4-(4-Chloroanilinomethyl)phenoxy]propanol, mp 81° to 83° C.

(7) 2-[4-(4-Chloroanilinomethyl)phenoxy]-2-methylpropanol, mp 92° to 93° C.

(8) Ethyl 2-[4-(4-chloroanilinomethyl)-2-methoxyphenoxy]-2-methylpropionate, mp 73° to 74° C.

(9) Sodium 2-[4-(4-chloroanilinomethyl)-2-hydroxyphenoxy]-2-methylpropionate, mp 121° to 125° C.

(10) 3,3-Dimethyl-7-(4-chloroanilinomethyl)-1,4-benzodioxan-2-one, mp 97° to 98° C.

EXAMPLE 4 (Process D)

(A) 11.7 g of 4-(4-chloroanilinomethyl)phenol and 16.8 g of powdery potassium hydroxide are suspended in 176 ml of acetone. To the suspension is added dropwise a solution of 10.7 g of 1-trichloromethyl-1-methylethanol in 8 ml of acetone, and the mixture is refluxed under heating for 5.5 hours. The reaction mixture is filtered and washed with acetone. The filtrate and washed liquid are combined together and distilled under reduced pressure to remove the acetone. 100 ml of water is added to the residue, and the aqueous solution is washed twice with 50 ml of diisopropyl ether. Over the aqueous solution is placed 150 ml of ethyl acetate, and the mixture is adjusted to pH 4 with 10% hydrochloric acid. The ethyl acetate layer is separated, whilst the aqueous layer is extracted with 50 ml of ethyl acetate. The extract is combined with the previously separated ethyl acetate solution, and the mixture is washed with a saturated aqueous solution of sodium chloride, dried over magnesium sulfate and distilled under reduced pressure to remove the solvent. To 15.6 g of the resulting residue is added 130 ml of 5% aqueous solution of sodium bicarbonate. The mixture is heated at 50° to 55° C. to dissolve the residue. The solution obtained is left to stand for cooling and then washed three times with 50 ml of ethyl acetate. Over the aqueous solution is placed 100 ml of ethyl acetate, the mixture is adjusted to pH 4, and the ethyl acetate layer is separated. The aqueous layer is extracted with 50 ml of ethyl acetate, and the extract and the separated ethyl acetate layer combined together are washed with a saturated aqueous solution of sodium chloride, dried over magnesium sulfate and then distilled under reduced pressure to remove the solvent to give 12.6 g of 2-[4-(4-chloroanilinomethyl)phenoxy]-2-methylpropionic acid, mp 160° to 162° C.

(B) In 10 ml of acetone are suspended 1 g of 4-(4-chloroanilinomethyl)phenol and 1.44 g of powdery potassium hydroxide, and 0.54 ml of chloroform is added dropwise to the suspension at room temperature. The mixture is stirred at 55° C. for 5.5 hours. The acetone is distilled off from the reaction mixture, water is added to the residue, and the aqueous solution obtained is washed with ether, adjusted to pH 4 with 10% hydrochloric acid and then extracted with ethyl acetate. The extract is back-extracted with a saturated aqueous solution of sodium bicarbonate, and the extract is adjusted to pH 4 with 10% hydrochloric acid and thereafter extracted with ethyl acetate again. The resulting extract is washed with water, dried and distilled under reduced pressure to remove the solvent. The residue is recrystallized from ethanol to give 0.8 g of 2-[4-(4-chloroanilinomethyl)phenoxy]-2-methylpropionic acid, mp 161° to 162° C.

(C) In 80 ml of dioxane is dissolved 2 g of 4-(4-chloroanilinomethyl)phenol, and 4.8 g of powdery potassium hydroxide is added to the solution with stirring. 3.04 g of 1-trichloromethyl-1-methylethanol is gradually added to the resulting solution. The mixture is stirred at 55° C. for 3 hours. The reaction mixture is distilled under reduced pressure to remove dioxane, and to the resulting residue is added water. The aqueous solution is washed with ether, then adjusted to pH 4 with 10% hydrochloric acid and extracted with ethyl acetate. The extract is back-extracted with 5% aqueous solution of sodium carbonate. The resultant extract is adjusted to pH 4 with 10% hydrochloric acid and extracted again with ethyl acetate. The ethyl acetate extract is washed with water, dried and distilled under reduced pressure to remove the solvent. The residue is washed with ethanol to give 0.74 g of 2-[4-(4-chloroanilinomethyl)phenoxy]-2-methylpropionic acid, mp 158° to 161° C.

(D) At room temperature, 18.6 g of tribromomethane is added dropwise to a solution of 10 g of 4-(4-chloroanilinomethyl)phenol, 50 ml of methyl ethyl ketone, 13.8 g of powdery potassium hydroxide in 100 ml of dioxane. The mixture is refluxed under heating for 5 hours and then distilled under reduced pressure to remove the solvent, and water is added to the residue. The solution is washed with ether, thereafter adjusted to pH 4 with 10% hydrochloric acid and extracted with ethyl acetate. The extract is washed with water and dried. The solvent is distilled off from the dried extract under reduced pressure, and the resulting residue is dissolved in an aqueous solution of 2.83 g of sodium bicarbonate in 100 ml of water at 50° C. The solution is washed twice with ethyl acetate. The aqueous layer is separated and adjusted to pH 4 with 10% hydrochloric acid and extracted twice with ethyl acetate. The extract is washed with water and dried. After distilling off the solvent from the dried extract, the residue is washed with diisopropyl ether. The precipitated crystals are collected by filtration to give 4.2 g of 2-{4-(4-chloroanilinomethyl)phenoxy}-2-methylbutyric acid, mp 152° to 153° C.

(E) The following compounds are obtained by using the similar procedures as those of the Examples 4 (A) to 4 (D).

(1) 2-{4-(4-Chloroanilinomethyl)phenoxy}propionic acid, mp 148° to 149° C.
(2) 2-[4-{N-(4-Chlorophenyl)-N-methylaminomethyl}phenoxy]-2-methylpropionic acid, mp 63° to 65° C.
(3) 2-[4-{N-(4-Chlorophenyl)-N-benzylaminomethyl}phenoxy]-2-methylpropionic acid, mp 65° to 67° C.

EXAMPLE 5 (Process E)

(A) A mixture of 6.27 g of 2-[4-(4-chloroanilinomethyl)-phenoxy]-2-methylpropionic acid, 120 ml of absolute ethanol and 2.2 g of concentrated sulfuric acid is refluxed under heating for 3 hours and 40 minutes. The ethanol is distilled off from the reaction mixture under reduced pressure. The residue is basified with a dilute aqueous solution of sodium bicarbonate, and the resulting solution is extracted three times with ether. The extract is washed with water once, then with a dilute aqueous solution of sodium bicarbonate twice and thereafter with water twice and is subsequently dried over magnesium sulfate. The dried extract is concentrated under reduced pressure, and the resulting oily concentrate is dissolved in ether. Ethanol and hydrochloric acid are added to the solution, and the precipitated crystals are collected by filtration, washed with ether and recrystallized from isopropyl alcohol to give 4.8 g of ethyl 2-[4-(4-chloroanilinomethyl)phenoxy]-2-methylpropionate hydrochloride in the form of colorless flakes, mp 143° to 146° C.

Elementary analysis: $C_{19}H_{23}NO_3Cl_2$ Calcd. C 59.38; H 6.03; N 3.68; Cl 18.45. Found C 59.29; H 6.00; N 3.80; Cl 18.57.

(B) In 100 ml of ethanol is dissolved 5.6 g of 2-[4-(4-chloroanilinomethyl)phenoxy]-2-methylbutyric acid, and 5.6 g of concentrated sulfuric acid is added to the solution. The mixture is refluxed under heating for 6 hours. After distilling off ethanol from the reaction mixture under reduced pressure, diisopropyl ether is added to the residue, and 20 ml of water and 22 ml of 20% aqueous solution of sodium carbonate are further added thereto with ice-cooling. The diisopropyl ether layer is separated from the mixture, and the aqueous layer is extracted with diisopropyl ether. The extract is combined with the previously separated diisopropyl ether solution, and the solution is washed with a saturated aqueous solution of sodium chloride, dried and the solvent is distilled off under reduced pressure. The oily residue is subjected to silica gel column chromatography by using benzene as developer. Concentration of the eluate under reduced pressure gives 2.3 g of ethyl 2-[4-(4-chloroanilinomethyl)phenoxy-2-methylbutyrate as a residue. The product is dissolved in ether, and 15% ethanol solution of hydrochloric acid is added to the solution. The precipitated crystals are collected by filtration to give 2 g of ethyl 2-[4-(4-chloroanilinomethyl)-phenoxy]-2-methylbutyrate hydrochloride, mp 135° to 137° C.

(C) The following compounds are obtained by using the similar procedures as those of the Examples 5 (A) to 5 (B).

(1) Ethyl 2-(4-anilinomethylphenoxy)-2-methylpropionate, mp 45° to 46° C.
(2) Ethyl 2-(4-anilinomethylphenoxy)-2-methylpropionate hydrochloride, mp 158° to 163° C.
(3) Ethyl 2-[4-(p-anisidinomethyl)phenoxy]-2-methylpropionate hydrochloride, mp 119° to 120° C.
(4) Ethyl 2-(4-cyclohexylaminomethylphenoxy)-2-methylpropionate hydrochloride, mp 140° to 142° C.

(5) Ethyl 2-(4-isobutylaminomethylphenoxy)-2-methylpropionate hydrochloride, mp 118° to 119° C.
(6) Ethyl 2-(4-benzylaminomethylphenoxy)-2-methylpropionate hydrochloride, mp 138° to 139° C.
(7) Ethyl 2-[4-(p-toluidinomethyl)phenoxy]-2-methylpropionate hydrochloride, mp 133° to 135° C.
(8) Ethyl 2-[4-(3-chloroanilinomethyl)phenoxy]-2-methylpropionate hydrochloride, mp 146° to 148° C.
(9) Ethyl 2-[4-{N-(4-chlorophenyl)-N-methylaminomethyl}-phenoxy]-2-methylpropionate, oil.

Infrared absorption spectrum (liquid film) 1730, 1280, 1235, 1175, 1140, 1020 cm$^{-1}$

(10) Ethyl 2-(4-ethylaminomethylphenoxy)-2-methylpropionate hydrochloride, mp 117° to 118° C.
(11) Ethyl 2-[4-{N-benzyl-N-(4-chlorophenyl)aminomethyl}-phenoxy]-2-methylpropionate hydrochloride, mp 137° to 141° C.
(12) Ethyl 2-{4-(4-chloroanilinomethyl)phenoxy}propionate, oil.

Infrared absorption sectrum (liquid film) 3410, 1740 cm$^{-1}$.

(13) N,N-bis[4-(1-methyl-1-ethoxycarbonylethoxy)benzyl]ethylamine hydrochloride, mp 164° to 165° C.
(14) Ethyl 2-[4-(1-pyrrolidinylmethyl)phenoxy]-2-methylpropionate, colorless oil.

Infrared absorption spectrum (liquid film) 1725, 1280, 1230, 1175, 1135, 1020 cm$^{-1}$.

(15) Ethyl 2-[4-(4-chloroanilinomethyl)-2-methoxyphenoxy]-2-methylpropionate, mp 73° to 74° C.

EXAMPLE 6 (Process F)

(A) A mixture of 6.14 g of ethyl 2-[4-(4-chloroanilinomethyl)phenoxy]-2-methylpropionate, 130 ml of 95% ethanol and 52 ml of 1 N aqueous solution of sodium hydroxide is stirred at 70° C. for 50 minutes. After concentrating the reaction mixture under reduced pressure, the residue is dissolved in water and the solution is washed with ether five times. To the aqueous solution is added 55 ml of 1 N hydrochloric acid with cooling, and the precipitated crystals are extracted twice with ether. The extract is washed with water twice, then dried over magnesium sulfate and thereafter the solvent is distilled off to give 5.6 g of 2-[4-(4-chloroanilinomethyl)phenoxy]-2-methylpropionic acid, colorless crystals, mp 155° to 158° C.

(B) In 50 ml of dried methanol are dissolved 10.0 g of ethyl 2-[4-(4-chloroanilinomethyl)phenoxy]propionate and 1.68 g of potassium hydroxide. The mixture is stirred at room temperature for 5 hours. After concentrating the reaction mixture, water is added to the residue, and the resulting solution is washed with ether. The aqueous layer is acidified with hydrochloric acid and extracted with ether. The extract is washed with water, then dried over magnesium sulfate and thereafter the solvent is distilled off. The resulting crystalline residue is recrystallized from benzene to give 8.0 g of 2-[4-(4-chloroanilinomethyl)phenoxy]propionic acid, mp 148° to 149° C.

(C) In 20 ml of ethanol is dissolved 1.2 g of ethyl 2-[4-{N-(4-chlorophenyl)-N-methylaminomethyl}-phenoxy]-2-methylpropionate. Subsequently, 15 ml of 1 N aqueous solution of sodium hydroxide is added to the solution, and the mixture is stirred at room temperature for 4 hours. After distilling off the ethanol from the reaction mixture under reduced pressure, the residue is dissolved in water. The solution is adjusted to pH 4 with 10% hydrochloric acid, and the precipitated crystals are collected by filtration and dried to give 0.94 g of 2-[4-{N-(4-chlorophenyl)-N-methylaminomethyl}-phenoxy]-2-methylpropionic acid, mp 63° to 65° C.

(D) In 40 ml of ethanol is dissolved 2.3 g of ethyl 2-[4-{N-(4-chlorophenyl)-N-benzylaminomethyl}-phenoxy]-2-methylpropionate, and 25 ml of 1 N aqueous solution of sodium hydroxide is added to the solution. The mixture is refluxed under heating for 2 hours. After concentrating the reaction mixture under reduced pressure, the residue is dissolved in water. The solution is adjusted to pH 4 with 10% hydrochloric acid. The resulting crystals are collected by filtration and dried to give 1.9 g of 2-[4-{N-(4-chlorophenyl)-N-benzylaminomethyl}phenoxy]-2-methylpropionic acid, mp 65° to 67° C.

(E) The following compounds are obtained by using the similar procedures of those of the Examples 6 (A) to 6 (D).

(1) 2-[4-(4-chloroanilinomethyl)phenoxy]-2-methylbutyric acid, mp 152° to 153° C.
(2) Sodium 2-[4-(4-chloroanilinomethyl)-2-hydroxyphenoxy]-2-methylpropionate, mp 121° to 125° C.
(3) 3,3-Dimethyl-7-(4-chloroanilinomethyl)-1,4-benzodioxan-2-one, mp 97° to 98° C.

EXAMPLE 7 (Process G)

(A) A solution of 2.0 g of ethyl 2-[4-(4-chloroanilinomethyl)phenoxy]propionate in 20 ml of ether is dropwise added to a suspension of 324 mg of lithium aluminum hydride in 20 ml of anhydrous ether over a period of 10 minutes under 10° C. The mixture is stirred for 20 minutes at room temperature and cooled under 10° C., and to the mixture is dropwise added 25 ml of 10% ammonium chloride aqueous solution. An insoluble material is filtered off and the ether layer is separated. The aqueous layer is extracted with ether and both of the ether layers are combined. The extract is washed with a saturated sodium chloride aqueous solution and dried, after which the solvent is distilled off. The residue is collected by filtration, washed with a mixture of n-hexane and diisopropyl ether and dried to give 1.42 g of 2-[4-(4-chloroanilinomethyl)phenoxy]propanol, mp 81° to 83° C.

Infrared absorption spectrum (nujol) 3250 cm$^{-1}$.

(B) A solution of 5 g of ethyl 2-[4-(4-chloroanilinomethyl)phenoxy]-2-methylpropionate in 50 ml of ether is dropwise added to a suspension of 775 mg of lithium aluminum hydride in 50 ml of anhydrous ether under 10° C. with stirring and the mixture is stirred for 2 hours at the same temperature. To the resultant mixture is dropwise added 60 ml of 10% ammonium chloride aqueous solution at 5° to 10° C. An insoluble material is filtered off and the ether layer is separated. The aqueous layer is further extracted with ether and both of the ether layers are combined. The combined ether solution is washed with a saturated sodium chloride aqueous solution and dried. The solvent is distilled off and the residue is washed with diisopropyl ether and dried to give 3.5 g of 2-[4-(4-chloroanilinomethyl)phenoxy]-2-methylpropanol, mp 84° to 91° C. This material is recrystallized from diisopropyl ether to give pure compound, mp 92° to 93° C.

Infrared absorption spectrum (nujol) 3250 cm$^{-1}$.
N.M.R. spectrum (CDCl$_3$, δ)

| ppm | 6.40–7.33 | (8H, m) |
| | 4.22 | (2H, s) |
| | 3.56 | (2H, s) |

| | | |
|---|---|---|
| 2.33 | (1H, broads) | |
| 1.24 | (6H, s) | |

EXAMPLE 8 (Process H)

A mixture of 1.25 g of 40% ethanol solution of ethylamine, 3.06 g of powdery potassium carbonate and 20 ml of absolute ethanol is cooled to 5° to 10° C. with stirring, and a solution of 6.68 g of ethyl 2-(4-bromomethylphenoxy)-2-methylpropionate in 7 ml of absolute ethanol is added dropwise to the resulting solution over a period of about 30 minutes. The mixture is stirred at room temperature for 2 hours, and 0.3 ml of 40% ethanol solution of ethylamine is added to the mixture. After stirring the mixture for 1 hour, the insolubles are removed by filtration and the filtrate is concentrated. The oily residue is dissolved in ether, and the ethereal solution is washed with water, dried and distilled to remove the ether. The residual oil (5.4 g) is dissolved in 30 ml of ether, and a mixture of hydrochloric acid and ethanol is added to the solution. After distilling off the solvent, a small amount of ether is added to the oily residue, which is solidified by triturating it with cooling. The solid is washed with ether and then collected by filtration to give 3.0 g of N,N-bis[4-(1-methyl-1-ethoxycarbonylethoxy)benzyl]ethylamine hydrochloride, mp 163° to 165° C. Recrystallization of the product from a mixture of ethanol and ether gives 2.0 g of a pure product, mp 164° to 165° C. On the other hand, the ether is distilled off from the filtrate previously prepared to obtain an oily product, which is solidified in an ether-isopropyl ether mixture and filtered to give 2.5 g of the object compound, mp 153° to 157° C. The crystals are recrystallized from a mixture of ethanol and ether to give crystals (1.9 g), which are further recrystallized to give 1.5 g of the object compound, mp 161° to 163° C.

Elementary analysis: $C_{28}H_{39}NO_6 \cdot HCl$ Calcd. C 64.42; H 7.72; N 2.68; Cl 6.79 Found C 64.37; H 7.69; N 2.85; Cl 6.89

EXAMPLE 9 (Process I)

(A) To 2.9 g of ethyl 2-[4-(4-chloroanilinomethyl)-phenoxy]-2-methylpropionate are added 10 ml of formaldehyde and 20 ml of formic acid to prepare a solution, which is stirred at room temperature for 30 minutes and then at 50° C. for 1 hour. The formaldehyde and formic acid are distilled off from the reaction mixture under reduced pressure, and ethanol is added to the residue. After filtering off the insolubles from the resulting solution, the ethanol is distilled off from the filtrate. The resulting oily residue is dissolved in ether, washed with water and dried. The ether is distilled off from the dried solution to given an oily residue (2.8 g), which is purified by silica gel column chromatography, using chloroform as an eluent to give 2.3 g of ethyl 2-[4-{N-(4-chlorophenyl)-N-methylaminomethyl}phenoxy]-2-methylpropionate, an oily product.

Infrared absorption spectrum (liquid film) 1730, 1280, 1235, 1175, 1140, 1020 cm$^{-1}$.

N.M.R. spectrum (CDCl$_3$, δ)

| ppm | 6.5–7.3 | (8H, m) |
|---|---|---|
| | 4.40 | (2H, s) |
| | 4.21 | (2H, q, J = 7Hz) |
| | 2.93 | (3H, s) |
| | 1.56 | (6H, s) |

| | 1.23 | (3H, t, J = 7Hz) |
|---|---|---|

(B) 3.47 g of benzyl bromide is added dropwise to a mixture of 6 g of ethyl 2-[4-(4-chloroanilinomethyl)-phenoxy]-2-methylpropionate hydrochloride, 3.24 g of potassium carbonate and 90 ml of dimethylformamide, and the resulting mixture is stirred at 60° C. for 3 hours. The reaction mixture is poured into 300 ml of ice-water and is extracted three times with 100 ml of ethyl acetate and twice with 50 ml of the same. The extract is washed with a saturated aqueous solution of sodium chloride and then dried. The solvent is distilled off from the dried extract, and the residue (7.5 g) is purified by column chromatography with 150 g of silica gel, using chloroform as a developer, to give 5.7 g of ethyl 2-[4-{N-(4-chlorophenyl)-N-benzylaminomethyl}phenoxy]-2-methylpropionate. The product is dissolved in 100 ml of ether, and dried hydrogen chloride gas is introduced into the solution. The resulting crystals are collected by filtration and recrystallized from isopropyl alcohl to give 4.3 g of ethyl 2-[4-{N-(4-chlorophenyl)-N-benzylaminomethyl}phenoxy]-2-methylpropionate hydrochloride, mp 137° to 141° C.

(C) The following compounds are obtained by using the similar procedures as those of the Examples 9 (A) to 9 (B).

(1) 2-[4-{N-(4-Chlorophenyl)-N-benzylaminomethyl}-phenoxy]-2-methylpropionic acid, mp 65° to 67° C.
(2) 2-[4-{N-(4-Chlorophenyl)-N-methylaminomethyl}-phenoxy]-2-methylpropionic acid, mp 63° to 65° C.
(3) N,N-bis[4-(1-Methyl-1-ethoxycarbonylethoxy)benzyl]-ethylamine hydrochloride, mp 164° to 165° C.

EXAMPLE 10 (Process J)

A mixture of 500 mg of ethyl 2-[4-(4-chloroanilinomethyl)-2-methoxyphenoxy]-2-methylpropionate, 206 mg of ethanethiol, 159 mg of 50% sodium hydride and 10 ml of dimethylformamide is heated at 100° C. for 3 hours. The reaction mixture is poured into ice-water and washed with ether. The aqueous layer is adjusted to pH 2 with 10% hydrochloric acid and extracted with ether. The extract is washed with water, dried and concentrated. The residue is pulverized with a mixture of diisopropyl ether and n-hexane and the crystals are collected by filtration to give 250 mg of 3,3-dimethyl-7-(4-chloroanilinomethyl)-1,4-benzodioxan-2-one, mp 97° to 98° C. From the mother liquor 60 mg of the same compound is further obtained.

Infrared absorption spectrum (nujol) 3400, 1760 cm$^{-1}$.

N.M.R. spectrum (CDCl$_3$, δ)

| ppm | 6.40–7.17 | (7H, m) |
|---|---|---|
| | 4.23 | (2H, s) |
| | 1.53 | (6H, s) |

To a solution of 158.7 mg of 3,3-dimethyl-7-(4-chloroanilinomethyl)-1,4-benzodioxan-2-one in 10 ml of ethanol is added 5 ml of a 1/10 N sodium hydroxide aqueous solution and the mixture is warmed to give clear solution. The solution is concentrated and the precipitated crystals are collected by filtration, washed with water and ether, and dried to give 140 mg of sodium 2-[4-(4-chloroanilinomethyl)-2-hydroxyphenoxy]-2-methylpropionate, mp 121° to 125° C.

Infrared absorption spectrum (nujol) 3500, 3400, 2650-2400, 1560 cm$^{-1}$.

What we claim is:

1. Substituted-phenyl substituted-alkyl ether of the formula:

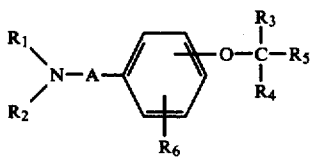

wherein
- $R_1$ is aryl or ar(lower)alkyl;
- $R_2$ is hydrogen, lower alkyl, aryl or ar(lower)alkyl;
- $R_3$ is lower alkyl;
- $R_4$ is hydrogen or lower alkyl;
- $R_5$ is carboxy or lower alkoxycarbonyl;
- $R_6$ is hydrogen, hydroxy or lower alkoxy; and
- A is lower alkylene; in which the aryl or the ar(lower)alkyl for $R_1$ and $R_2$ may be substituted with halogen, hydroxy or lower alkoxy; and pharmaceutically acceptable salts thereof.

2. The compound of claim 1, wherein $R_5$ is carboxy.

3. The compound of claim 2 having the following formula:

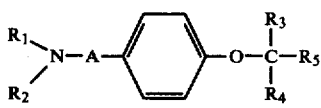

wherein $R_1$ is aryl substituted with halogen, $R_2$ is hydrogen, lower alkyl or ar(lower)alkyl, $R_3$ is lower alkyl, $R_4$ is hydrogen or lower alkyl, $R_5$ is carboxy and A is lower alkylene; and pharmaceutically acceptable salt thereof.

4. The compound of claim 3, wherein $R_4$ is lower alkyl.

5. The compound of claim 4, wherein $R_2$ is hydrogen.

6. The compound of claim 5, wherein
- $R_1$ is phenyl substituted with halogen,
- $R_3$ is methyl,
- $R_4$ is methyl or ethyl, and
- A is methylene.

7. The compound of claim 6, wherein $R_1$ is 4-chlorophenyl.

8. The compound of claim 7, wherein $R_3$ and $R_4$ are both methyl.

9. The compound of claim 7, wherein
- $R_3$ is methyl, and
- $R_4$ is ethyl.

10. The compound of claim 4, wherein $R_2$ is lower alkyl or ar(lower)alkyl.

11. The compound of claim 10, wherein $R_1$ is phenyl substituted with halogen.

12. The compound of claim 1, wherein
- $R_1$ is 4-chlorophenyl,
- $R_2$ is methyl or benzyl,
- $R_3$ and $R_4$ are both methyl, and
- A is methylene.

13. The compound of claim 12, wherein $R_2$ is methyl.

14. The compound of claim 12, wherein $R_2$ is benzyl.

15. The compound of claim 3, wherein
- $R_1$ is phenyl substituted with halogen,
- $R_2$ is hydrogen,
- $R_4$ is hydrogen and
- A is methylene.

16. The compound of claim 15, wherein
- $R_1$ is 4-chlorophenyl and
- $R_3$ is methyl.

17. The compound of claim 1, wherein $R_5$ is lower alkoxycarbonyl.

18. The compound of claim 17 having the following formula:

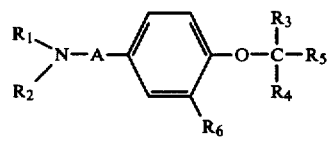

wherein
- $R_1$ is aryl or ar(lower)alkyl;
- $R_2$ is hydrogen, lower alkyl or ar(lower)alkyl;
- $R_3$ is lower alkyl;
- $R_4$ is hydrogen or lower alkyl;
- $R_5$ is lower alkoxycarbonyl;
- $R_6$ is hydrogen, hydroxy or lower alkoxy;
- and A is lower alkylene; in which the aryl for $R_1$ may be substituted with lower alkoxy or halogen; and pharmaceutically acceptable salt thereof.

19. The compound of claim 18, wherein $R_6$ is hydrogen.

20. The compound of claim 19, wherein $R_4$ is lower alkyl.

21. The compound of claim 20, wherein $R_2$ is hydrogen.

22. The compound of claim 21, wherein $R_1$ is phenyl which may be substituted with halogen or lower alkoxy, tolyl or benzyl.

23. The compound of claim 22, wherein
- $R_1$ is phenyl, 3-chlorophenyl, 4-chlorophenyl, 4-methoxyphenyl, p-tolyl or benzyl;
- $R_3$ and $R_4$ are both methyl,
- $R_5$ is ethoxycarbonyl, and
- A is methylene.

24. The compound of claim 23, wherein $R_1$ is phenyl and its hydrochloride.

25. The compound of claim 23, wherein $R_1$ is 3-chlorophenyl and its hydrochloride.

26. The compound of claim 23, wherein $R_1$ is 4-chlorophenyl and its hydrochloride.

27. The compound of claim 23, wherein $R_1$ is 4-methoxyphenyl and its hydrochloride.

28. The compound of claim 23, wherein $R_1$ is p-tolyl and its hydrochloride.

29. The compound of claim 23, wherein $R_1$ is benzyl and its hydrochloride.

30. The compound of claim 22, wherein
- $R_1$ is phenyl substituted with halogen,
- $R_3$ is methyl,
- $R_4$ is ethyl,
- $R_5$ is ethoxycarbonyl, and
- A is methylene.

31. The compound of claim 30, wherein $R_1$ is 4-chlorophenyl and its hydrochloride.

32. The compound of claim 19, wherein
- $R_1$ is aryl substituted with halogen,
- $R_2$ is hydrogen, and
- $R_4$ is hydrogen.

33. The compound of claim 32, wherein
R$_1$ is phenyl substituted with halogen.
34. The compound of claim 33, wherein
R$_1$ is 4-chlorophenyl,
R$_3$ is methyl,
R$_5$ is ethoxycarbonyl, and
A is methylene.
35. The compound of claim 20, wherein
R$_1$ is aryl substituted with halogen, and
R$_2$ is lower alkyl or ar(lower)alkyl.
36. The compound of claim 35, wherein
R$_1$ is phenyl substituted with halogen,
R$_2$ is methyl or benzyl,
R$_3$ and R$_4$ are both methyl,
R$_5$ is ethoxycarbonyl, and
A is methylene.
37. The compound of claim 36, wherein
R$_1$ is 4-chlorophenyl.
38. The compound of claim 37, wherein
R$_2$ is methyl.
39. The compound of claim 37, wherein
R$_2$ is benzyl and its hydrochloride.
40. The compound of claim 18, wherein
R$_1$ is aryl substituted with halogen,
R$_2$ is hydrogen,
R$_4$ is lower alkyl, and
R$_6$ is lower alkoxy.
41. The compound of claim 40, wherein
R$_1$ is phenyl substituted with halogen.
42. The compound of claim 41, wherein
R$_1$ is 4-chlorophenyl,
R$_3$ and R$_4$ are both methyl,
R$_5$ is ethoxycarbonyl,
R$_6$ is methoxy, and
A is methylene.
43. The compound of claim 2 having the following formula:

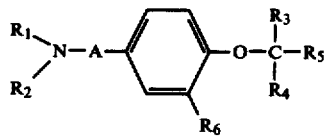

wherein
R$_1$ is aryl substituted with halogen,
R$_2$ is hydrogen,
R$_3$ is lower alkyl,
R$_4$ is lower alkyl,
R$_5$ is carboxy,
R$_6$ is hydroxy, and A is lower alkylene, and pharmaceutically acceptable salt thereof.
44. The compound of claim 43, wherein
R$_1$ is phenyl substituted with halogen.
45. The compound of claim 44, wherein
R$_1$ is 4-chlorophenyl,
R$_3$ and R$_4$ are both methyl, and
A is methylene
and its sodium salt.

* * * * *